United States Patent [19]

Seppi et al.

[11] Patent Number: 5,168,532
[45] Date of Patent: Dec. 1, 1992

[54] METHOD FOR IMPROVING THE DYNAMIC RANGE OF AN IMAGING SYSTEM

[75] Inventors: Edward J. Seppi, Portola Valley; Edward G. Shapiro, Mountain View; John M. Pavkovich, Palo Alto, all of Calif.

[73] Assignee: Varian Associates, Inc., Palo Alto, Calif.

[21] Appl. No.: 547,451

[22] Filed: Jul. 2, 1990

[51] Int. Cl.⁵ .......................... H04N 3/14; G06K 9/20
[52] U.S. Cl. ................................ 382/50; 358/213.13; 358/213.19
[58] Field of Search ............. 358/211, 213.13, 213.19, 358/213.28, 213.31, 228; 382/50

[56] References Cited

U.S. PATENT DOCUMENTS

| 3,983,398 | 9/1976 | Boyd | 378/14 |
|---|---|---|---|
| 4,149,247 | 4/1979 | Pavkovich et al. | 382/6 |
| 4,149,248 | 4/1979 | Pavkovich | 382/6 |
| 4,149,249 | 4/1979 | Pavkovich | 378/901 |
| 4,158,854 | 6/1979 | Duinker | 358/111 |
| 4,164,657 | 8/1979 | Duinker et al. | 358/111 |
| 4,168,435 | 9/1979 | Duinker | 358/111 |
| 4,266,136 | 5/1981 | Duinker | 378/21 |
| 4,399,464 | 8/1983 | Hix et al. | 358/213.13 |
| 4,547,676 | 10/1985 | Suzuki et al. | 358/213.19 |
| 4,597,014 | 6/1986 | Suzuki | 358/213.13 |
| 4,647,975 | 3/1987 | Alston et al. | 358/213.13 |
| 4,701,626 | 10/1987 | Ishizaki et al. | 358/213.19 |
| 4,734,776 | 3/1988 | Wang et al. | 358/213.31 |
| 4,819,075 | 4/1989 | Imaide et al. | 358/213.19 |

FOREIGN PATENT DOCUMENTS 1579265 11/1980 United Kingdom .

OTHER PUBLICATIONS

D. P. Boyd, et al., "Engineering Status of Computerized Tomographic Scanning", Sep. 2, 1976; Optical Engineering, Jan-Feb. 77/vol. 16, No. 1, pp. 37-44.
Norman A. Baily, "Acquisition of Quantitive Physiological Data and Computerized Image Reconstruction Using a Single Scan TV System", Stanford conference 1975, pp. 149-156.
Norman A. Baily, "Computerized Tomography Using video Techniques", Aug. 23, 1976, Optical Engineering, Jan.-Feb., 77/vol. 16, No. 1, pp. 23-27.
Sturm, et al., "Quantitative Three-Dimensional Dynamic Imaging of Structure and Function of the cardiopulmonary and Circulatory Systems in all Regions of the Body", 1975, Society of Photo-optical Instrumentation Engineers, Palos Verdes Estates, CA. 1975.
Bernard E. Oppenheim, M.D., "More Accurate Algorithms for Interactive 3-Dimensional Reconstruction", 1974, IEEE Transactions on Nuclear Science, vol. NS-21, Jun. 1974, pp. 72-77.
Bracewell et al., "Image Reconstruction Over a Finite Field of View", 12 Jul. 1975, Journal of the Optical Society of America, vol. 65, No. 11, pp. 1342-1346.
Robb et al., "Three-Dimensional Reconstruction and Display of the Working Canine Heart and Lungs by Multiplanar S-Ray Scanning Videopensitometry", 1974, Brookhaven National Laboratory, Upton, New York, Jul. 16-19, 1974, pp. 99-106.
Douglas P. Boyd, "Status of Diagnostic X-Ray CT: 1979", IEEE Transactions on Nuclear Science, vol. NS-26, No. 2, Apr. 1979, pp. 2836-2839.

(List continued on next page.)

Primary Examiner—Leo H. Boudreau
Assistant Examiner—David Fox
Attorney, Agent, or Firm—Peter J. Sgarbossa

[57] ABSTRACT

Disclosed is a method for improving the dynamic resolution of an imaging system. The method employs a dual sampling or exposure technique which samples light from an image intensifier over a long and a short sample interval. When the resulting measurement for the long sample interval exceeds a threshold level, the short sample interval measurement is used, multiplied by a scaling factor. Below the threshold the long sample interval is used.

10 Claims, 31 Drawing Sheets

OTHER PUBLICATIONS

Gordon L. Brownell, "New Instrumentation for Computerized Tomography", 1976, Proceedings of the Conference on Computerized Tomography in Radiology, St. Louis, Mo., Apr. 25-28, 1976, pp. 15-22.

Herman, et al., "Reconstruction Using Divergent-Ray Shadowgraphs", 1977, University park Press, pp. 105-117.

B. E. Oppenheim, "reconstruction Tomography from Incomplete Projects", 1977, University Park Press, pp. 155-183.

Huang, et al., "Effect of Out-of-field Objects in Transaxial Reconstuction Tomography", 1977, University Park Press, pp. 185-198.

"Characteristics and Use of PCD Linear Image Sensors", Hamamatsu Technical Information, SD-03, cover page and p. 9.

| DETECTOR NUMBER | ACTUAL ANGLE FOR RESPONSE | DESIRED ANGLE FOR RESPONSE (Δ = 0.048°) |
|---|---|---|
| 0 | −11.995 | −12° |
| 1 | −11.899 | −11.952 |
| 2 | −11.820 | −11.904 |
| 3 | −11.728 | −11.856 |
| ⋮ | ⋮ | ⋮ |
| 510 | +11.870 | +11.952 |
| 511 | +11.970 | +12° |

| PHOTODIODE NUMBER | POLYNOMIAL 1 $C_{10}$ $C_{11}$ $C_{12}$ $C_{13}$ $C_{14}$ | POLYNOMIAL 2 $C_{20}$ $C_{21}$ $C_{22}$ $C_{23}$ $C_{24}$ | POLYNOMIAL 3 $C_{30}$ $C_{31}$ $C_{32}$ $C_{33}$ $C_{34}$ |
|---|---|---|---|
| 0 | | | |
| 1 | | | |
| 2 | | | |
| 3 | | | |
| ... | | | |
| 542 | | | |
| 543 | | | |

$$W_1 = \begin{cases} 0, & C_2 < 0 \\ 1, & C_1 > 1 \\ C_1, & 0 \le C_1 \le 1 \end{cases}$$

$$W_3 = \begin{cases} 0, & C_3 < 0 \\ 1, & C_3 > 1 \\ C_3, & 0 \le C_3 \le 1 \end{cases}$$

$$W_2 = 1 - W_3 \Big|_{det.} - W_1 \Big|_{det.}$$

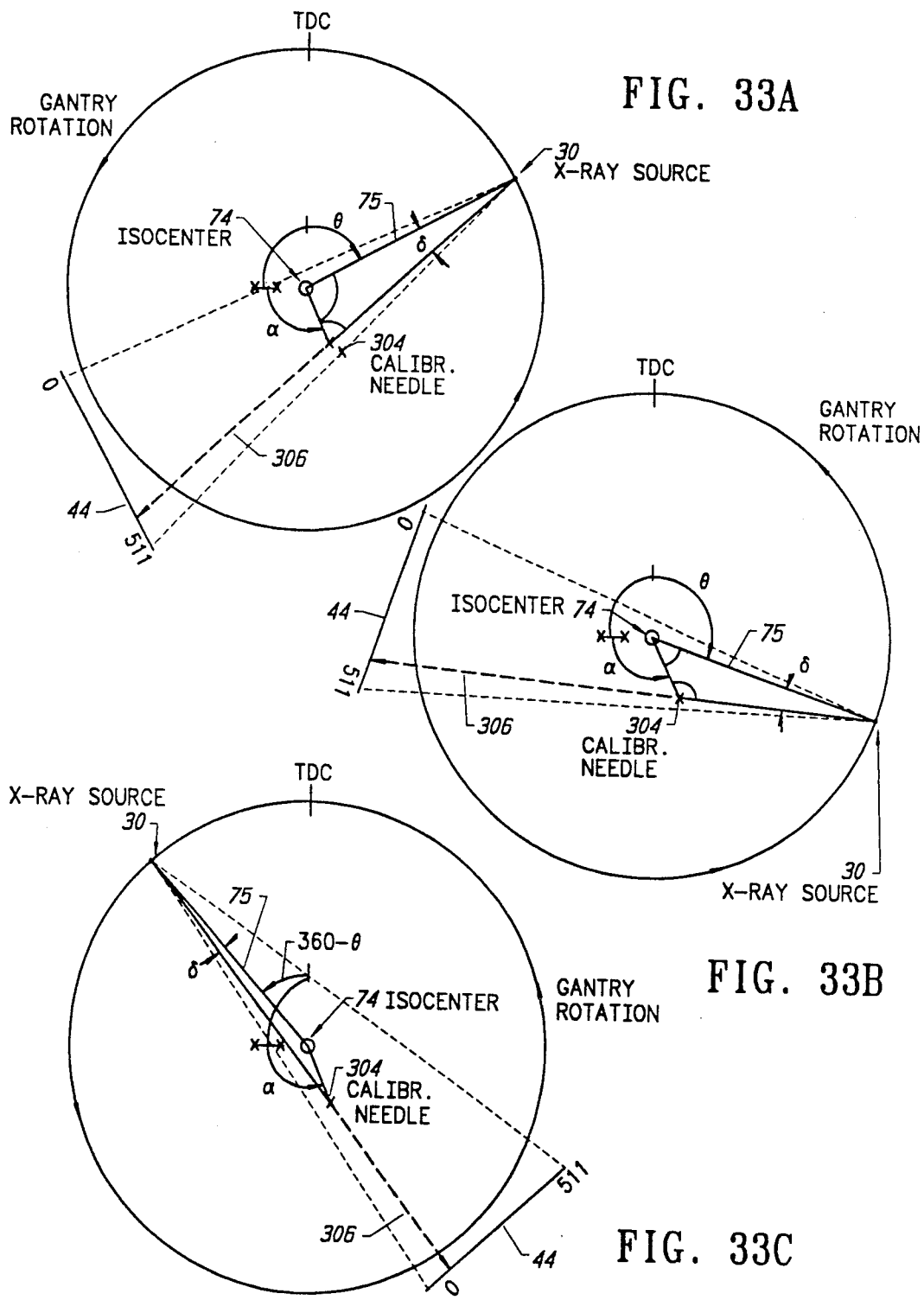

METHOD FOR IMPROVING THE DYNAMIC RANGE OF AN IMAGING SYSTEM

MICROFICHE APPENDIX

Included as part of this application is Microfiche Appendix A, consisting of six microfiche sheets containing 76 frames.

FIELD OF THE INVENTION

This invention pertains to a method for improving the dynamic range in computed tomography systems which incorporates an image intensifier detector to aid in the formation of better images.

CROSS REFERENCE

Reference is made to copending U.S. patent application entitled "Partial Fan-beam Tomographic Apparatus and Data Reconstruction Method", filed even date herewith and assigned to the same assignee as the subject application.

BACKGROUND OF THE INVENTION

In recent years, much interest has been evidenced in a field now widely known as computed tomography. In a typical procedure utilizing computed tomography (or CT), an X-ray source and detector are physically coupled together on opposite sides of the portion of a sample which is to be examined. The sample can be a patient or phantom or other objects, for example. X-rays are made to transit through the sample to be examined, while the detector measures the X-rays which make it through the sample without being absorbed or deflected. Periodically, the paired source and detector are rotated to differing angular orientations about the sample, and the data collection process repeated.

A very high number of measurements of attenuation values may be obtained by procedures of this type. The relatively massive amounts of data thus accumulated are processed by a computer, which typically does a mathematical data reduction to obtain attenuation values for a very high number of transmission valves (typically in the hundreds of thousands) within the section of the sample being scanned. This data may then be combined to enable reconstruction of a matrix (visual or otherwise) which constitutes an accurate depiction of the density function of the sample section examined.

By considering one or more of such sections, skilled medical diagnosticians may diagnose various body elements such as tumors, blood clots, cysts, hemorrhages and various abnormalities, which heretofore were detectable, if at all, only by much more cumbersome and, in many instances, more hazardous-to-the-patient techniques.

CT Scanners

While apparatus of the aforementioned type have represented powerful diagnostic tools, and were deemed great advances in the radiography art, apparatus of the first generation suffered from many shortcomings. Acquisition of the raw data frequently entailed an undesirably long period, which among other things subjected a patient to both inconvenience and stress. The patient's inability to remain rigid for such a lengthy period, also could lead to blurring of the image sought to be obtained.

In U.S. Pat. No. 4,149,248, to John M. Pavkovich, entitled *Apparatus and Method for Reconstructing Data*, and assigned to the same assignee as is the present patent, apparatus and methodology are disclosed which alleviate a number of the prior art problems, most notably the lengthy period that was previously required for computer processing of the raw data provided by the detectors. The apparatus disclosed therein utilizes a fan beam source of radiation coupled with application of a convolution method of data reduction, with no intervening reordering of fan rays, to thereby eliminate the errors and delays in computation time which would otherwise be involved in such reordering. The radiation source and the detector means are positioned on opposite sides of the portion of the patient to be examined and these elements are made to rotate through a revolution or portion thereof about the patient. During such rotation, the detectors measure the radiation absorption at the plurality of transmission paths defined during the rotational process. In order to measure analog signals over a wide dynamic range, application-specific conversion schemes are usually employed. That is, when the signal-to-noise ratio of the input transducer exceeds that of the analog-to-digital converter, then input signal preprocessing is typically used to compress the input signal.

X-ray CT scanners are now a common tool for the diagnostic radiologist. Typically these are expensive, i.e. greater than a million dollars. These systems typically have scan times of 1 to 2 seconds with 0.3 mm spatial resolution. Density resolution as low as 0.25%, with degraded spatial resolution, is achievable. The technology of generator/detector design and the improvements in the microcomputer area over the past 10 years have enabled image detection and processing to approach real time.

Radiation Therapy Simulators

Radiation therapists often attempt to use scans from diagnostic CT scanners in planning a radiation therapy treatment. Because high levels of radiation are used during radiation therapy treatment it is important that the therapists be able to precisely locate the site to be treated. However, the relative position of organs within the body during a diagnostic CT scan are not the same as when a patient is placed on a flat couch of the radiation therapy machine. This occurs because the diagnostic CT scanner couch is more crescent shaped. Therefore, radiation therapy simulators have come into use. These simulators have patient couches that are identical to couches of radiation therapy machines. Also, in the simulator, the X-ray focal spot for fluoroscopic/radiographic imaging is positioned to allow the same target-to-patient isocenter as in the therapy machine. Beam shaping devices and other accessories can be added which attempt to exactly duplicate the therapy setup. Thus, simulators yield a projected planar image of the patient anatomy that is much more geometrically compatible with the position of the radiation therapy system. In addition to the properly oriented radiographic information, if cross-sectional CT images could be obtained at the same time, then the therapist would be further aided in planning the treatment.

A radiation therapy simulator is a diagnostic imaging X-ray machine shaped to simulate the geometry of radiation therapy (or radiotherapy) treatment units. Thus, a simulator includes an X-ray imaging source, a gantry to support and position the X-ray imaging source, a couch to support the patient, and an image forming system.

The dimensions of the gantry are such that it positions the x-ray imaging source relative to the couch in a geometry mathematically similar to the geometry of the radiotherapy machine. Images formed on the imaging system can then be interpreted in terms of the geometry of the radiotherapy machine. Images can be taken from different angles to aid in the planning of how to form the radiotherapy beam to maximize dose to the target and minimize damage to healthy organs.

In existing simulators, because the geometry of the simulator attempts to very closely simulate that of the radiotherapy machine, the X-ray imaging source and image forming system are limited to a configuration which is less than optimal for the quality of the image. Both the source and the image-detector-part of the image forming system are far from the patient. The image at the detector has been recorded on film.

An image intensifier has been used to increase the brightness of the image which can be used to produce a television image. A computer has been used to process and enhance the television image.

Computed Tomography Simulators

In the prior art, it is known to form a computed tomography image based on data obtained from a TV camera using an image intensifier tube (IIT) between the patient and a television camera. The output signal from the television camera is processed to form a digital signal which is further processed in a computer to form a tomographic image. This prior art system employing the television camera produces a noisy image of marginal value in simulation and planning.

Similar CT attempts using X-ray image intensifiers with video cameras have been made in the past by various groups. However, from prior CT experience, it is believed that the use of video camera signals based on data off the IIT was one of the major limiting features in these designs. Compared to the IIT, conventional video cameras have horizontal spatial resolution of 3-4 line pairs per mm over a 30 cm field, but their intensity output is both limited and nonlinear. Typically, tube video camera instantaneous signal dynamic range is limited to only two or three orders of magnitude. Conventional solid state video cameras have good linearity spatially and in intensity, but their signal dynamic range is also limited to about 1,000:1 at room temperature and with averaging lines possibly 4000:1.

In order to maintain X-ray photon statistics on a 16" (40 cm) diameter body, a detector with a minimum signal to noise ratio (S/N) of at least 200,000:1 is necessary. This is assuming a typical surface dose of 2 rads/scan and no compensating bolus around the patient. It is also necessary that the IIT, lens optics and photo detector yield an X-ray to electron quantum efficiency of greater than unity.

Medical or industrial X-ray CT applications typically require a detector system with millimeter spatial resolution and photon-limited intensity resolution. The rate of photons emitted from an X-ray source is statistical and follows a Poisson distribution. Thus, any ideal measurement of photon intensity has a root-mean-square (rms) noise equal to the square root of the average number of photons detected. Therefore, the detector system must have a total quantum detection efficiency (QDE) greater than unity in order to maintain photon statistics. Also, since additional random noise adds in quadrature, then the detector electronics must have a rms input noise level below the photon noise.

OBJECTIVES OF THE INVENTION

It is a primary objective of the present invention to provide a method for improving the dynamic range of a radiotherapy simulator system.

SUMMARY OF THE INVENTION

These objectives of the invention and other objectives, features and advantages will become apparent in the following specification and drawings. Briefly stated, the simulator comprises a computerized tomography capability based on use of an image intensifier tube (IIT) as the x-ray photon to visible light photon converter, typically a 12" IIT. Incident x-ray photons are absorbed by a thin (0.3 mm) cesium iodide (CsI) scintillator on the face of the IIT. The CsI crystals emit light photons which are converted to electrons by the photocathode of the IIT. The electrons are then accelerated and focused onto a phosphor at the exit window of the IIT for conversion back into light photons. The quantum detection efficiency (QDE) of this process is characterized by a 4-5 orders of magnitude ($10^4$ to $10^5$) increase in light photons to incident x-ray photons. The overall QDE of the measurement system is very dependent on the efficient collection of these light photons at the IIT output. A two-lens system has been implemented to collect and focus the light output from the IIT. The light collection efficiency of this lens system is proportional to the transmission and the square of the numerical aperture (f-stop). When both lenses are focused at infinity their light collection efficiency is approximately 1%, depending on the f-stop setting of the second lens. Accordingly, the IIT to light detector QDE in this case is still 2-3 orders of magnitude ($10^2$ to $10^3$) above unity.

The lenses focus the light output from the IIT onto a linear array of a multiplicity of photodiodes which produce output signals proportional to the incident light. Electronic signal processing means condition the photodiode output signals for use in constructing a tomographic x-ray image corresponding to the geometry of the radiation therapy simulator machine.

In accordance with the method of the present invention, charge accumulated by photodiodes are sampled using a long and a short sampling interval. When the magnitude of the visible light output from the IIT exceeds a threshold value, the measurement from the short sampling interval is used. Conversely, when the magnitude is less than the threshold value, the measurement from the long sampling interval is used.

When the measurement from the short interval is used, it is multiplied by a scaling factor. This scaling factor is determined with a calibration light source by comparing the long interval measurement to the short interval measurement. The scaling factor is then adjusted to obtain a best least squares fit between the long interval measurement and the scaled short interval measurement.

The threshold value for use of the short interval measurement is selected to be at a point close to but less than the saturation level for the photodiodes. In practice, the transition between use of the short interval measurement and the long interval measurement is made by using a weighted combination of the long interval sample and the short interval sample.

In the one embodiment of the invention, a transition range of sample magnitudes is defined, and for sample magnitudes below the transition range, the long interval measurement is used. For sample magnitudes above the transition range, the scaled short interval measurement is used. Finally for sample magnitudes within the transition range the weighted combination is used.

The conditioning performed by the electronic signal processing means includes linearizing the detector signals from the linear array. This involves the use of a plurality of n-th order polynomials, each of which is valid for a different range of magnitudes for signals from the photodiodes. Coefficients for these polynomials are determined by "least squares" curve fitting response data from photodiodes of the linear array to response data from a normalizing photodiode. In one embodiment, the different n-th order polynomials are valid for overlapping ranges, and for detector signals falling within the overlap, weighted combinations of values from the nth-order polynomials which are valid for the overlap are used as the linearized detector signal.

An imaging extension detector array is provided for use in extending the scan circle diameter. The imaging extension detector array is positioned at one edge of the image intensifier tube and detects x-ray photons directly. Each detector in the imaging extension detector array includes a body of scintillating crystal and a photodiode. Signals from the imaging extension detector array are conditioned by electronic signal processing means.

The electronic signal processing means includes means for accommodating a wide range of detector signal magnitudes from both IIT and extension detector photodiodes. These include an integrating preamplifier circuit for amplifying charge received from the photodiodes which has a reset and clamp arrangement which minimizes offset errors and enhances the dynamic range of the electronic signal processing means. Low noise conditions are achieved by phase locking the sampling by the integrating preamplifier, and subsequent digitization of the signal, to the line voltage from which the x-ray source and the system as a whole receives primary power.

Also included in the signal conditioning by the electronic signal conditioning means are an apparatus and method for compensating for background noise and point spread function effects. The background noise is measured with no illumination on the photodetectors, and is subtracted out of the detector signals during a scan.

As to point spread function effects, it has been discovered that in an IIT, optics, and photodetector imaging chain, a significant output level will exist for photodiodes in the photodetector which are not intentionally being illuminated. This is due, in part, to defocusing of electrons in the IIT, defocusing and scatter of light photons in the optics, and internal reflections within the optics. The point spread function effects are measured by causing selected ones of the photodiodes to be illuminated by selectively illuminating the image intensifier tube, and then reading the output levels of all photodiodes in the array. The output level for the illuminated photodiode is zeroed out, and the remaining output levels are used to form a correction matrix to deconvolve the detector readings taken during an actual scan.

BRIEF DESCRIPTION OF THE DRAWINGS

FIGS. 33A, 33B, and 33C illustrate how different positions of X-ray source 30 cause different detectors in photodiode linear array to be affected by a ray occluded by the calibration needle.

Lexicon

The following is a partial list of the lexicon used in the following description:

ABS: Automatic Brightness System
ADC: Analog to Digital Converter
CdWO$_4$: Cadmium Tungstate
$C_{ij}$: Polynomial Coefficient for the ith polynomial and the jth order factor in the polynomial
CsI: Cesium Iodide
CT: Computed Tomography
DET.: Actual Detector Measurement
DET.': Actual Detector Measurement Corrected for Photodiode Non-linearities
DMA: Direct Memory Access
FAD: Focus to Axis (Isocenter) Distance
FID: Focus to Intensifier Distance
F.S.A.D.: Focal Spot to Access Distance
IIT: Image Intensifier Tube
LED: Light Emitting Diode
Pb: Lead
PSF: Point Spread Function
RAM: Random Access Memory
RMS: Root Mean Square
TDC: Top Dead Center
WORM: Write Once Read Many

DESCRIPTION OF TH PREFERRED EMBODIMENTS

Figure 1:
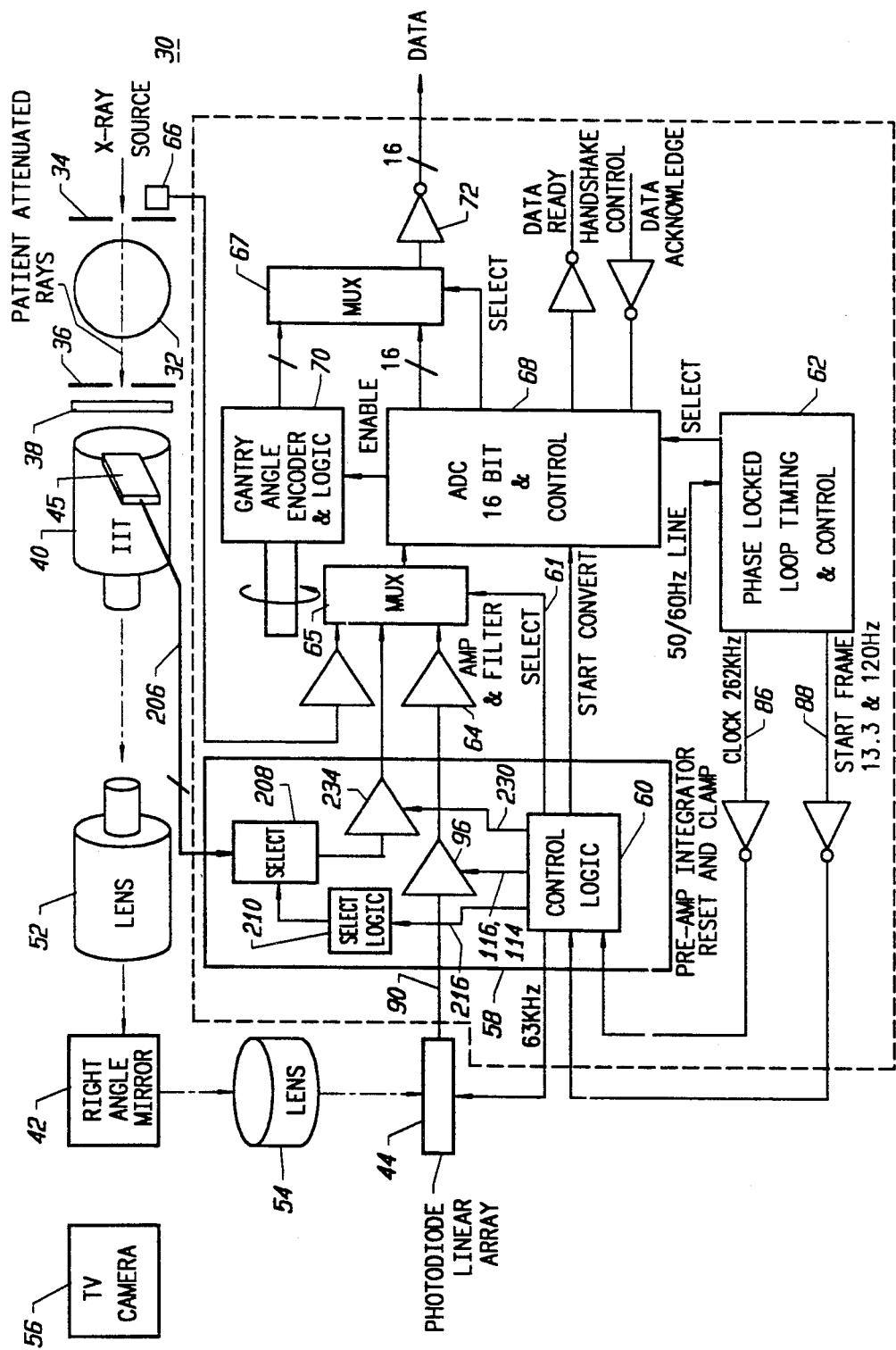
FIG. 1 shows a block diagram of the detector system of the invention.

Referring to FIG. 1, in the simulator of the present invention an object of interest is scanned to provide a series of projections at different selected angles about a rotational axis of the object. The projections are formed by passing a full or partial fan of radiation through the object of interest at each of these selected angles. For each projection, the object-attenuated fan of radiation is applied to an image intensifier tube which converts radiation photons to visible light photons. The visible light photons are then detected using a photodiode linear array. Signals from the photodiode linear array are conditioned and then converted into digital form. The digital information is then processed under computer control to correct the data for background noise, non-linearities in the image intensifier tube and photodiode array, point spread in the imaging chain; and for other effects. Thereafter, the corrected data from each of the projections is used to reconstruct an image of the cross section of the object of interest for that scan. Multiple scans can be taken to provide a three-dimensional view of the object of interest. These scans can then be displayed on a monitor with variations in the image being displayed representing different absorption coefficients or absorption densities. The reconstructed image can also be stored in digital form for later viewing.

The use of a full or a partial fan-beam of x-ray radiation depends upon the diameter of the object being scanned and the dimensions of the detector electronics available. For example, where a 12" image intensifier tube is used, and a scan of the head of a patient is desired, a full fan-beam is used. As such, the centers of the fan-beam, the head of the patient, and the image intensifier tube, are aligned along a common axis.

On the other hand, when the body of a patient is to be scanned, and a 12" image intensifier tube is used, the diameter of the body is too large to be fully contained within the 12" width of the tube. As such, a partial fan-beam is used, with the image intensifier tube offset from the axis along which the fan-beam and the patient centers lie.

Imaging Extension Embodiment

In a further embodiment of the present invention, an imaging extension is provided by which the maximum patient scan circle diameter is increased, for example, from 40 to 50 cm when a 30 cm (12") image intensifier tube is used. It allows for an increase in patient to gantry clearance from 60 cm to 77 cm, and also allows for a full 48 cm wide patient couch to be used.

When a 12-inch image intensifier tube is used without the imaging extension, the maximum size object which can be scanned is limited by the image intensifier tube diameter and its distance from the x-ray source.

Full Fan Versus Partial Fan Beams

Figure 2:
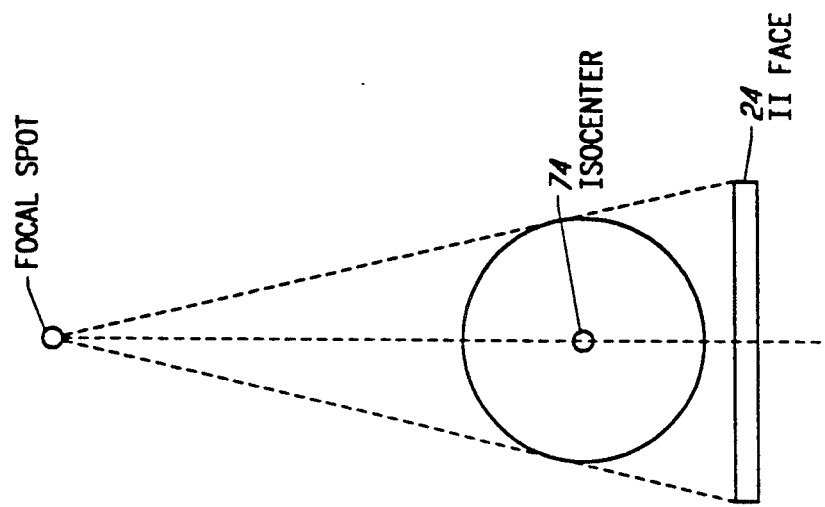
FIG. 2 shows a diagram of the reconstruction diameter for a head scan.

The 12-inch image intensifier tube active area varies from unit-to-unit, but typically has been 28 cm ±1 cm across the face at 135 cm from the x-ray source. For a full-fan, head-scan centered at 100 cm, as seen in FIG. 2, this geometry limits the maximum size object to 21 cm diameter. This covers approximately 95% of the U.S. male population according to Diffrient's Humanscale publication. (See N. Diffrient et al., *Humanscale* 11213 *Manual*, 1979, The MIT Press.) Most diagnostic CT scanners have a 25 cm maximum head scan circle which allows for approximately 100% population coverage and less critical patient positioning.

Both head and body scans can be increased in size by using an asymmetric (or partial) x-ray fan-beam. The simulator head scan circle can be increased to 25 cm by using an asymmetric verses full-fan approach. In this mode the image intensifier tube is shifted a few cm off center and a 360 degree scan is performed. Thus, a larger area is covered compared to the full-fan mode. Some loss in contrast and spatial resolution results because the entire object is not viewed in each projection.

The projection data is then reconstructed using a variation of the Pavkovich fan-beam reconstruction method, described in copending patent application entitled "Partial Fan-beam Tomographic Apparatus and Data Reconstruction Method", filed even date herewith, and assigned to the assignee of the subject application.

Figure 7:
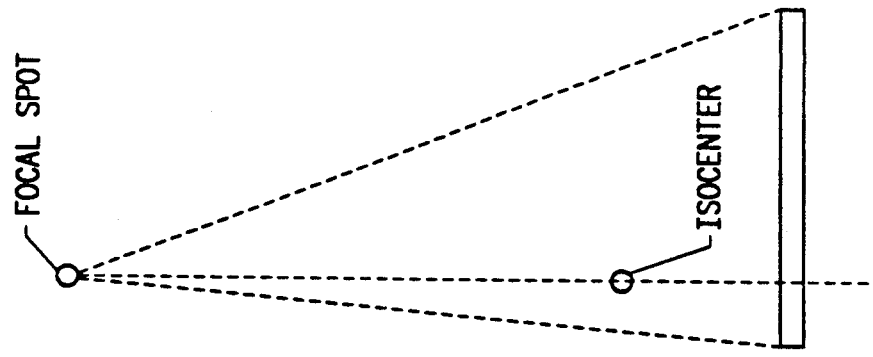
FIG. 7 shows a diagram of the reconstruction diameter for a body scan.

In the case of body scans, the image intensifier tube is shifted to the maximum extent. The largest body scan with the above arrangement is less than 40 cm diameter as depicted in FIG. 7. This covers approximately 95% of the U.S. males across the chest, but less than 50% across the shoulders. The majority of the diagnostic scanners have a 50 cm maximum body scan which covers 97% of the same population.

Radiation Treatment Simulator—Details

In one application, the present invention is used in conjunction with a radiation treatment simulator and planning system.

Radiation treatment simulator and planning systems ("simulator") simulate the geometry and movement of megavoltage radiation therapy equipment. The following are the basic items into which the simulator system can be divided: floor mounted drive unit with rotating arm, X-ray head and crosswire assembly, detector including image intensifier, treatment couch, relay frame, and control units. Many of the basic simulator system elements suitable for use with the present invention can be found in the Ximatron CR Radiotherapy Simulator System, manufactured by Varian, the assignee of the subject application.

Drive Unit

Figure 4:
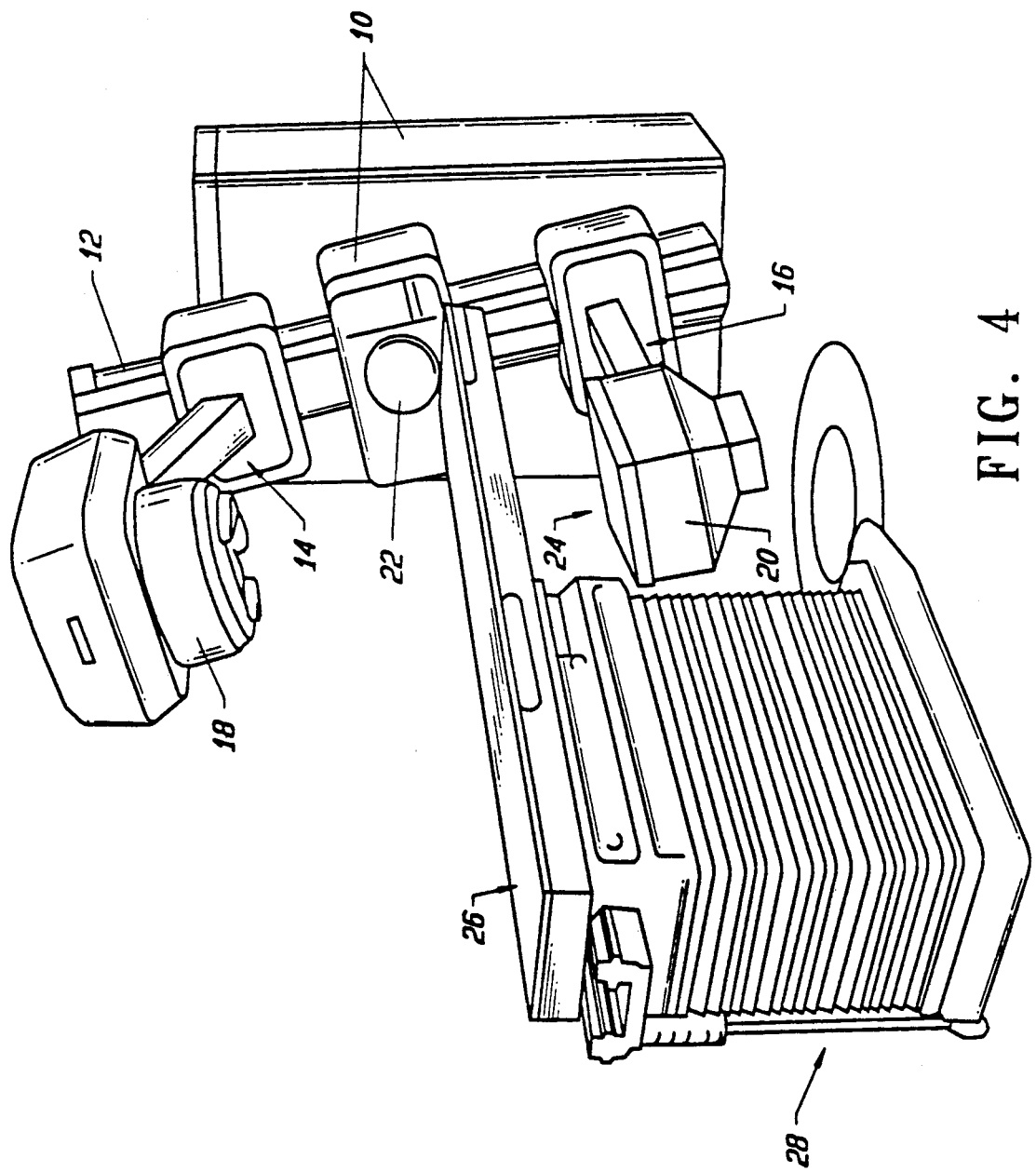
FIG. 4 shows a simplified perspective view of a radiation treatment simulator in conjunction with which the present invention can be used.

Referring to FIG. 4, typically, the drive unit 10 comprises a welded steel fabrication which is bolted on a plinth, which is preferably cast in the floor, prior to the completion of the final floor finish. The drive structure houses the variable speed electric drive unit and a high precision slewing ring bearing on which is fitted the rotating arm 12. On the arm 12 are mounted the carriages 14 and 16 for the X-ray head assembly 18 and the image intensifier tube assembly 20, respectively. Attached to the front of the arm is a circular disk 22, the circumference of which carries a scale mark in degrees from 0.0 to 360.0 degrees. A screen wall (not shown) is supplied which carries the zero data mark for the scale together with a small sub-scale for ease of reading if the zero data is visually obstructed. The screen wall is built into a partition wall which seals off the drive unit and control gear from the room, thus presenting a clean finish.

X-ray Head 18

Protruding through the top of the arm 12 is the X-ray head assembly 18 which is carried on a rigidly constructed steel fabrication. The X-ray system on the simulator has a generator having an output of 125 kVp and 300 mA (radiographic mode) or 125 kVp and 30 mA (fluoroscopic mode), in conjunction with a double focus (0.6 mm and 1 mm) X-ray tube, with a permanent 2 mm element and filter. The X-ray tube is mounted in a yoke on the end of the steel fabrication.

Mounted below the tube is a lead-bladed collimator which can be manually set to give field sizes from 0 to 35 by 35 cm and 100 cm F.S.A.D. The collimator also contains a lamp operated by a switch on the side of the housing, which will define the area of the X-ray beam through the blades onto the patient's skin.

Mounted with and in front of the collimator is a crosswire assembly. This is fitted with two pairs of motorized tungsten wires to give any square or rectangular field from 4×4 cm to 30×30 cm at 100 cm F.S.A.D. Windows inside of the crosswire housing have scales fitted indicating the field sizes at 100 cm. These are repeated on electrical indicators fitted in the remote control console. The collimator and crosswire assembly have motorized and manual rotation over the range ±45°. A suitable scale is provided for reading the angular position. The complete head is capable of being electrically driven from its maximum F.S.A.D. of 100 cm down to 60 cm.

Detector 20

Protruding through the front bottom of the arm 12 is the image intensifier tube assembly 20. This unit is mounted on a double carriage to enable scanning over an area of ±18 cm about the center of the X-ray beam both longitudinally and laterally. The complete assembly is also capable of being electrically driven from a maximum of 50 cm from the rotation axis to the image intensifier tube face 24, down to 10 cm. Anti-collision bars fitted to the image intensifier tube face 24 will, when operated, isolate the electrical supplies to the operating motors. Provision is made to override the anti-collision interlocks in order to drive out of the collision situation.

Treatment Couch 26

The couch assembly 26 includes a steel framework supported on a large precision bearing ring. These are mounted in a pit cast in the floor. The framework carries the telescopic ram assembly 28 for the couch 26 together with a circular floor section. The bearing allows the couch 26 to be isocentered ±100° about the X-ray beam, either electrically or manually. A scale is fitted around the edge of the pit for positioning.

The telescopic ram assembly 28 provides vertical movement of the couch top from a minimum height of 60 cm to a maximum of 120 cm.

Attached to the top of the telescopic ram is a sub-chassis which provides for manually lateral movement. A manual brake is provided by levers on either side of the couch, to lock the top in its set position. Fitted to this sub-chassis is a side channel couch top having a width of 50 cm and a length of 213 cm. This is fitted for motorized longitudinal movement of 123 cm and provision for manual override to facilitate rapid setting. Manual rotation of the couch top of the telescopic ram assembly is provided. The manual brake is provided to lock the top to its desired position.

A cushion top is provided with three removable sections giving clear openings of 43×31 cm. An overall transparent plastic film provides patient support when the cushions are removed. A removable head cushion is provided to expose a drill plate suitable for mounting head clamps, etc.

The System—Generally

Figure 5:
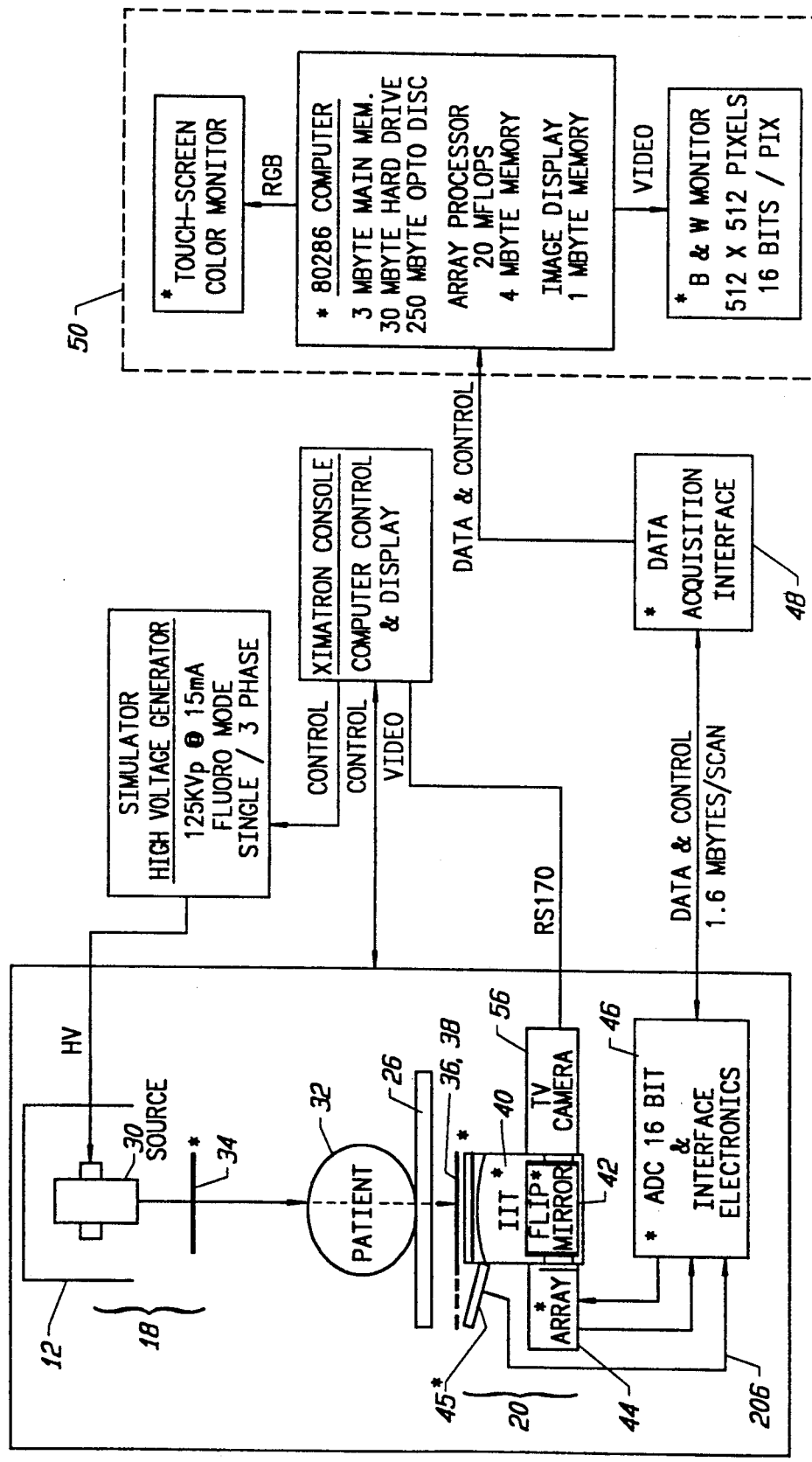
FIG. 5 is a block diagram which illustrates the elements (indicated by a "*") of the present invention which can be added to a radiation treatment simulator system to obtain a CT simulator system in accordance with the present invention.

Referring now to FIGS. 1 and 5, a computerized tomography system according to the invention is shown. FIG. 1 is a block diagram which illustrates the data gathering elements of the present invention in relation to an X-ray source 30 and patient 32. FIG. 5 is a block diagram which illustrates the elements (indicated by a "*") of the present invention which are added to the above referenced Ximatron simulator system to obtain a CT simulator system in accordance with the present invention.

In FIG. 5, it can be seen that the additional elements include: pre-patient collimator 34, post-patient collimator 36, grid 38, image intensifier tube 40, right angle flip mirror 42, photodiode linear array 44, imaging extension 45, 16-bit ADC and interface electronics 46, data acquisition interface 48, and a processing and display computer 50.

Data Acquisition Path

Referring now to FIG. 1, an x-ray source 30 passes radiation through a pre-patient collimator 34, then through the patient 32, then through a post-patient collimator 36 and anti-scatter grid 38 to an image intensifier tube 40 (IIT) and imaging extension 45.

The image from image intensifier tube 40 is projected onto a photodiode linear array 44 using first lens 52, right angle mirror 42 and second lens 54. When the right angle mirror is 42 swung out of the way, the image from the image intensifier tube 40 can be viewed with a television camera 56.

Signals from the photodiode array 44 and imaging extension 45 are sent, on command, to a pre-amp, integrator, reset and clamp circuit 58. Control logic circuitry 60 in the preamp, integrator, reset and clamp circuit 58 provides timing signals, which are in turn derived from clocks provided by a phase locked loop timing and control circuit 62. Circuit 62 is synchronized to the 50/60 Hz line frequency. Control signals and light intensity signals are sent from the pre-amp, integrator, reset and clamp circuit 58 through an amplifier and filter 64, multiplexed in multiplexer 65 with signals from an x-ray normalization detector 66, and signals from imaging extension detector array 45, to the analog-to-digital converter and control circuit 68 (ADC). The ADC 68 sends an enable signal to a gantry angle encoder and logic circuit 70, and both send signals to the data processing computer 50 (FIG. 5), via an optically isolated data path 72 and multiplexer 67 in a time-multiplexed manner. The computer 50 returns handshake signals to the ADC 68.

Selected individual portions of the above system will now be discussed in greater detail.

Pre-patient and Post-patient Collimators 34 and 36

Figure 3:
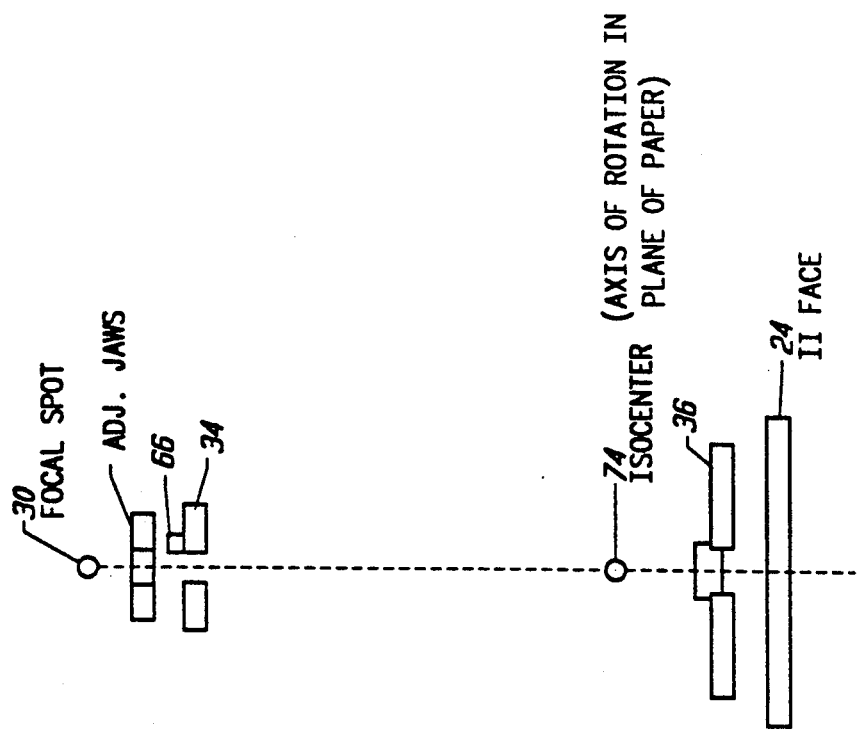
FIG. 3 shows a side view diagram of simulator geometry for a head CT.
Figure 6:
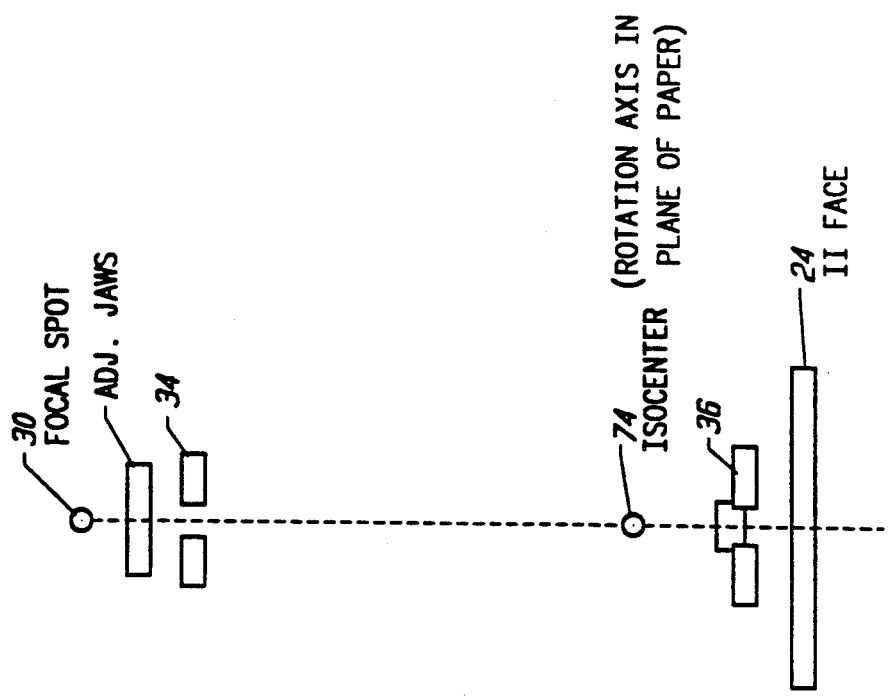
FIG. 6 shows a side view diagram of simulator geometry for a body CT.

Pre-patient collimator 34 provides the primary collimation of the fan beam that is incident on the object of interest. These collimators are typically constructed of lead ("Pb"), are configured to be removable, and typically provide a beam width at the isocenter 74 of between 0.5 cm and 1.0 cm. Referring to FIGS. 2, 3, 6, and 7, typical dimensional relationships are illustrated (without the imaging extension 45) between the X-ray source 30, the pre-patient collimator 34, the center of rotation of the patient 32 ("isocenter"), the post-patient collimator 36, and the image intensifier tube face 24. FIGS. 3 and 2 illustrate these dimensional relationships for a full fan-beam "head" scan. FIGS. 6 and 7 illustrate these dimensional relationships for a partial fan-beam "body" scan.

For a "head" scan, referring to FIGS. 3 and 2, it can be seen that the focal spot of the X-ray source 30 is positioned approximately 100 cm from the isocenter 74, and the image intensifier tube face 24 is positioned approximately 32 cm from isocenter 74. FIG. 3 is taken transverse to the width of the beam, so that the axis of rotation of the rotating arm 12 is in the plane of the paper. FIG. 2 is taken looking across the width of the beam so that the axis of rotation of the rotating arm 12 is coming out of the plane of the paper.

Positioned in the x-ray beam are beam dimension adjustment jaws 76, followed by pre-patient collimator 34 at approximately 65 cm from the focal spot of X-ray source 30. X-ray normalization detector 66 is positioned on the x-ray source side of the pre-patient collimator 34. The post-patient collimator 36 is positioned just above the image intensifier tube 40.

For a "head" scan, a full fan-beam is used with a beam thickness of approximately 5 mm (at isocenter 74). See FIG. 3. The image intensifier tube face 24 is centered in the beam. Given the above separation of X-ray source 30, isocenter 74, and image intensifier tube face 24, pre-patient collimator 34 has a slit width of approximately 6 mm. Post-patient collimator 36 has a slit width of approximately 8 mm. Beam dimension adjustment jaws 76 are set to provide a beam thickness at pre-patient collimator 34 wide enough to illuminate x-ray normalization detector 66, and to provide a beam width which is approximately 21.1 cm at the isocenter 74 (see FIG. 2). Further, beam dimension adjustment jaws 76 are positioned close enough to pre-patient collimator 34 so that the latter is the primary collimator of the beam.

For a "body" scan, a partial fan-beam is used, with a beam width of approximately 1 cm used at the isocenter 74. As can be seen in FIG. 6, pre-patient collimator 34 is positioned between 55-65 cm from the focal spot of X-ray source 30, and has a slit width of approximately 6 mm. The image intensifier tube face 24 is positioned approximately 35 cm from the isocenter 74. Post-patient collimator 36 has a slit width of approximately 13 mm. As can be seen in FIG. 7, with the axis of rotation of the rotating arm 12 coming out of the plane of the paper, the image intensifier tube face 24 is offset from center, and the beam dimension adjustment jaws 76 are set so that a partial fan-beam is generated. For example, the beam from the pre-patient collimator 34 would illuminate the image intensifier tube face 24 edge-to edge, but the portion of the beam passing through the isocenter 74 would be incident approximately 3 cm from one edge of the image intensifier tube face 24. See FIG. 7.

In angular terms, the beam would have an outer edge approximately 1.27 degrees from a center line 75 running between the focal spot of the X-ray source 30 and the isocenter 74, and its other outer edge at approximately 10.49 degrees from the center line 75.

In the current embodiment, the slice thickness for head scans is 5 mm at isocenter, F.I.D. is 147 cm. For body scans the current slice thickness is 1 cm at isocenter, with an F.I.D. at 147 cm. This provides additional patient scan circle clearance.

A 14:1 cylindrically focused grid is included in the post-patient collimation 36.

The pre-patient collimator 34 gives a well defined fan which helps to reduce patient dose and scatter. It also carries the beam shaping filters which attenuate the peripheral portions of the x-ray beam which pass through thinner portions of the patient 32. This not only reduces patient dose but also reduces the dynamic range over which the IIT 40 and photodiode linear array 44 must respond.

Dimensional Relationships With Imaging Extension 45

Figure 8:
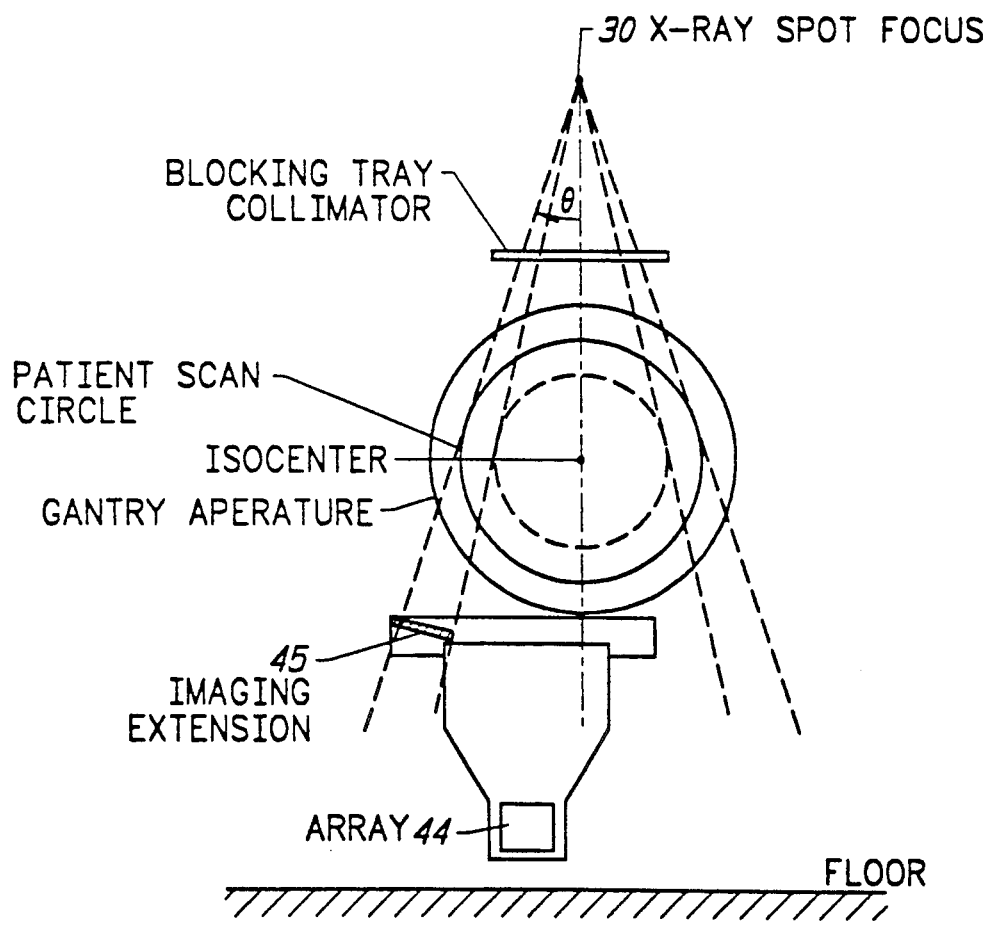
FIG. 8 shows the addition of an imaging extension detector array to the IIT which can be used to increase the scan circle diameter of the present invention.

FIG. 8 illustrates the dimensional relationship when the imaging extension 45 is used. In such a configuration, a partial fan beam can be used for a 50 cm patient scan circle. The pre-patient collimator 34 is positioned between 59-63 cm from the X-ray source 30; and the isocenter is approximately 100 cm from the X-ray source 30. The image intensifier tube face 24 is positioned approximately 147 cm from the X-ray source 30; and the most vertical point of imaging extension 45 is approximately 8.5 cm above the image intensifier tube face 24.

X-ray Normalization Detector 66

Returning to FIG. 1, the x-ray normalization detector 66 is mounted to one side of the slit in the pre-patient collimator 34 and provides readings of source intensity which are used to normalize x-ray tube output variations during the scan. The x-ray normalization detector 66 measures the unattenuated x-ray beam flux, allowing the detector to sample quite a large solid angle of the beam. X-ray normalization detector 66 is formed by combining a scintillating cadmium-tungstate ($CdWO_4$) crystal with a silicon photodiode. Preferably, the crystal measures $6 \times 6$ mm by 3 mm thick. Additional details of the crystal material, photodiode, and construction are provided hereinbelow in the discussion of the imaging extension detector array 45.

IIT 40 and Light Collection Optics 84

Figure 9:
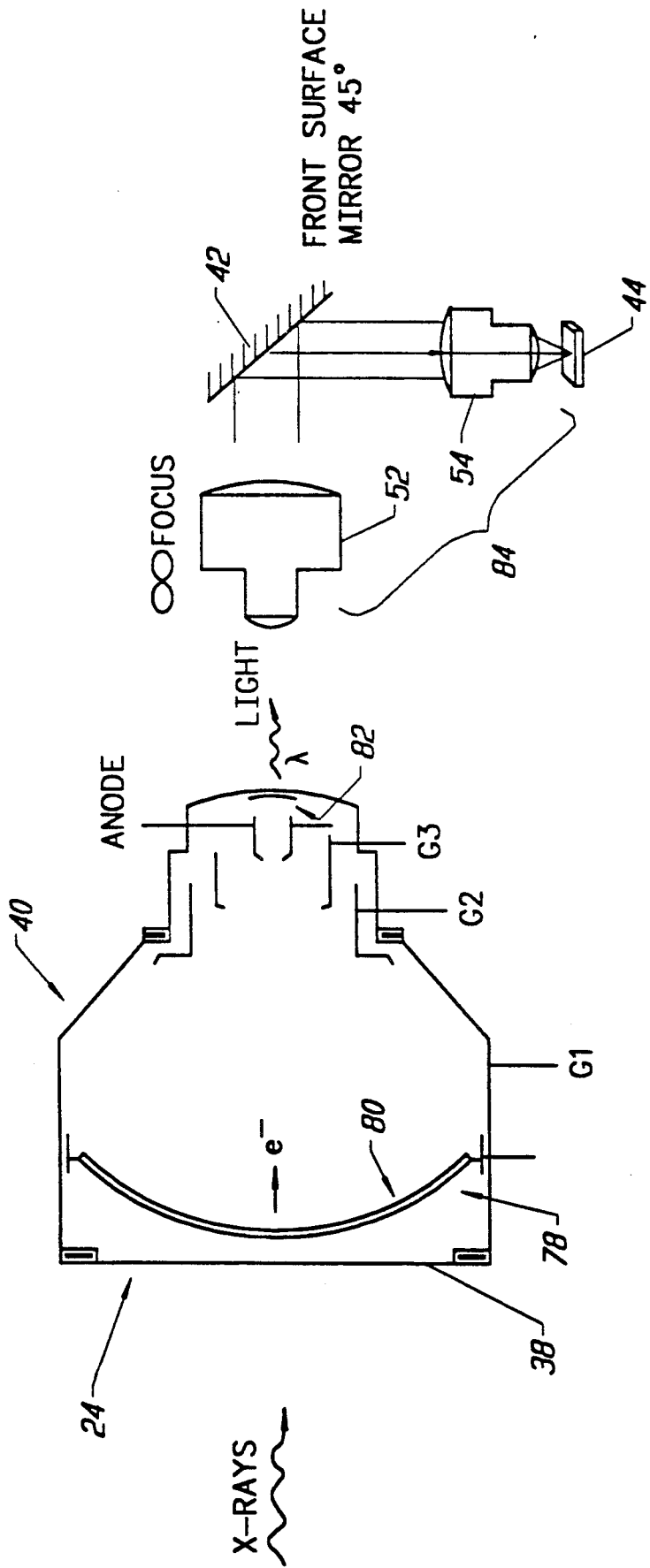
FIG. 9 provides a cross sectional view of a typical image intensifier tube, and the associated optics of the present invention.

The 12-inch image intensifier tube (IIT) 40 is a conventional medical image intensifier and serves as an X-ray photon to visible light photon converter. FIG. 9 provides a cross sectional view of a typical image intensifier tube, and the associated optics of the present invention. Incident X-ray photons are absorbed by the thin 0.3 mm CsI (cesium-iodide) scintillator 78 on the image intensifier tube face 24. The CsI crystal emits light photons which are converted to electrons by the attached photocathode 80. The electrons are accelerated and focused by focusing grids G1, G2 and G3, onto the output phosphor 82 for light conversion. The quantum efficiency of this process is characterized by a 4 to 5 order of magnitude ($10^4$ to $10^5$) increase in light photons to incident X-ray photons.

The CsI scintillator 78 is typically 12 mils thick. The output phosphor 82 is preferably "P20" type (ZnCdS). The accelerating voltage is typically between 30-35 kV. A one inch diameter image is produced at the output of image intensifier tube 40. Lead post-patient collimator 36 (FIG. 1) and anti-scatter grid 38 are used to define the CT slice thickness and to reduce X-ray scatter. The post-patient collimator 38 arrangement is mounted on a circular aluminum plate which is then bolted onto the mounting ring of the IIT 40.

The overall QDE of the measurement system is dependent on the efficient collection of these light photons at the IIT output phosphor 82. The light collection optics 84 which views the IIT output is a lens system as shown in FIGS. 1 and 9. The light collection efficiency for this lens geometry is proportional to the transmission and the square of the numerical aperture. With both lenses 52 and 54 focused at infinity, their light collection efficiency is approximately 1%, depending on the f-stop setting of the second lens. The IIT to light detector QDE in this case is still 2 to 3 orders of magnitude ($10^2$ to $10^3$) above unity.

In one embodiment of the present invention, first lens 52 is a conventional 82 mm lens set at a 1.2 f-stop and focused at infinity; and second lens 54 is a conventional 80 mm lens set at a 5.6 f-stop and focused at infinity.

In order to allow both the fluoro TV camera 56 and the photodiode linear array 44 to be permanently mounted, a dual port distributor with a motorized 45 degree flip mirror 42 is used, and is mounted on the IIT 40 in place of the standard distributor. The flip mirror 44 normally rests in the fluoro position and when the CT mode is selected, the mirror is flipped through 90 degrees so that the IIT light output is directed onto the linear detector array 44 through second lens 54.

Photodiode Linear Array 44

A variety of solid-state arrays have been evaluated for their suitability as light detectors of image data from the IIT. The requirements for the light detector in this system are: compatible spectral sensitivity, a wide signal dynamic range, i.e. 100,000:1, and sufficient spatial resolution for image reproduction. Compatible geometrical dimensions are also necessary to permit easy coupling of the photodiode linear array 44 to the output of the IIT 40.

A commercially available 512 channel linear silicon diode array meets these requirements and has yielded excellent results. This array is linear image sensor number S2301, manufactured by Hamamatsu of Hamamatsu City, Japan. The array is 1 inch (25.6 mm) in length and 2.5 mm in width. Each diode detector is 50 microns by 2.5 mm with 72% active area. With the IIT output image at one inch in diameter, a 1to-1 arrangement light collection optics 84 is used between the IIT 40 and the array 44. The photodiode linear detector array 44 is built into a camera housing which is mounted at one of the exit windows of the right angled flip mirror 42.

The normalized photon response of the array is greater than 60% from 475 to 875 nanometers and overlaps the IIT output phosphor spectrum. The IIT light output spectrum from the "P20" phosphor peaks at 532 nm. Thus, the silicon photodiode spectral response is a reasonable match to the "P20" phosphor curve. The QDE for silicon is approximately 0.6–0.7 electrons/photon. Therefore, from the above, the overall QDE ratio of incident X-ray photon to electron-hole pairs in silicon is still much greater than unity for the system as a whole.

To obtain a spatial resolution of 1 mm on an object, the detector must have a sufficient number of channels to permit one to digitize the image. The photodiode linear array 44 has 512 channels, which translates to 0.6 mm per detector at the image intensifier tube face 24 for a 12 inch tube. Tests and specifications on the image intensifier tube 40 have indicated that its spatial resolution is approximately 3.5 line pairs/mm over the 12-inch diameter, which exceeds the diode array's equivalent 0.9 line pairs/mm. Therefore, projected to the object, 1 mm resolution is possible in the reconstructed image data.

The photodiode linear array 44 is a 512 channel linear device with each channel capable of accumulating 22 pico coulombs of charge during an exposure. The noise characteristics of the commercial array and preamp is specified as 3500 electrons rms. The saturation level to noise ratio yields a single measurement maximum signal to noise ratio of 39,000:1.

The point spread response of the image intensifier tube 40 indicates a dynamic signal range of at least 100,000:1. However, the single channel dynamic range of the photodiode linear array 44 has been measured to be only 35,000:1 when used with the manufacturer's preamp. Thus, using a single measurement, the photodiode linear array 44 does not have sufficient dynamic range to match the IIT 40 output.

Dynamic Range Improvements

In accordance with the present invention, a dual exposure time scheme is employed, along with some additional improvements in the charge preamplifier circuitry, to permit the 100,000:1 signal range of IIT 40 to be utilized. A new preamplifier integrator design provides a 50,000:1 range at room temperature. The combination of the dual exposure time scheme and new preamplifier integrator design provides an array-preamp dynamic range of 400,000:1, or 19 bits total, for each channel, over a measurement interval of 100/83 msec (50/60 Hz) while maintaining photon statistics.

The improvements in dynamic range are obtained in part by minimizing of the effect of the charge amplifier reset noise in the preamplifier, by phase locking the measurement to the line frequency, and by using an analog amplification scheme to amplify the signal from photodiode linear array 44 prior to converting it to digital form.

Phase Locking to the Line Frequency

One source of degradation in the dynamic range of the measurement electronics is line frequency related ripple and harmonics in the x-ray source. The ripple and harmonics are a by-product of the rectification of the line voltage used in generating the high voltage CW for the x-ray source.

As can be seen in FIG. 1, phase locked loop timing and control circuit 62 provides a number of clocks which are synchronized to the line frequency. More specifically, phase locked loop timing and control circuit 62 includes a voltage controlled oscillator (not shown) which is operating at a preselected multiple of the line frequency and which is synchronized to the line frequency. Within phase locked loop timing and control circuit 62 are divider circuits which divide down the voltage controlled oscillator signal into a sampling clock 86 and a start frame clock 88. In the embodiment shown in FIG. 1, the sampling clock 86 is 262KHz and the start frame clock includes a 13.3 Hz component and a 120 Hz component. These clocks are applied to pre-amp integrator, reset and clamp circuit 58. As will be described hereinbelow, these clocks are used in the sampling of the photodiode linear array 44 and the dual exposure time scheme. Furthermore, phase locked timing and control circuit 62 supplies a select signal to analog-to-digital converter and control circuit 68 to synchronize its operation. When the timing in the measurement electronics is phase-locked in the above manner, substantial rejection of the line frequency ripple and harmonics can be obtained.

Pre-amp, Integrator, Reset and Clamp Circuit 58

Figure 10A:
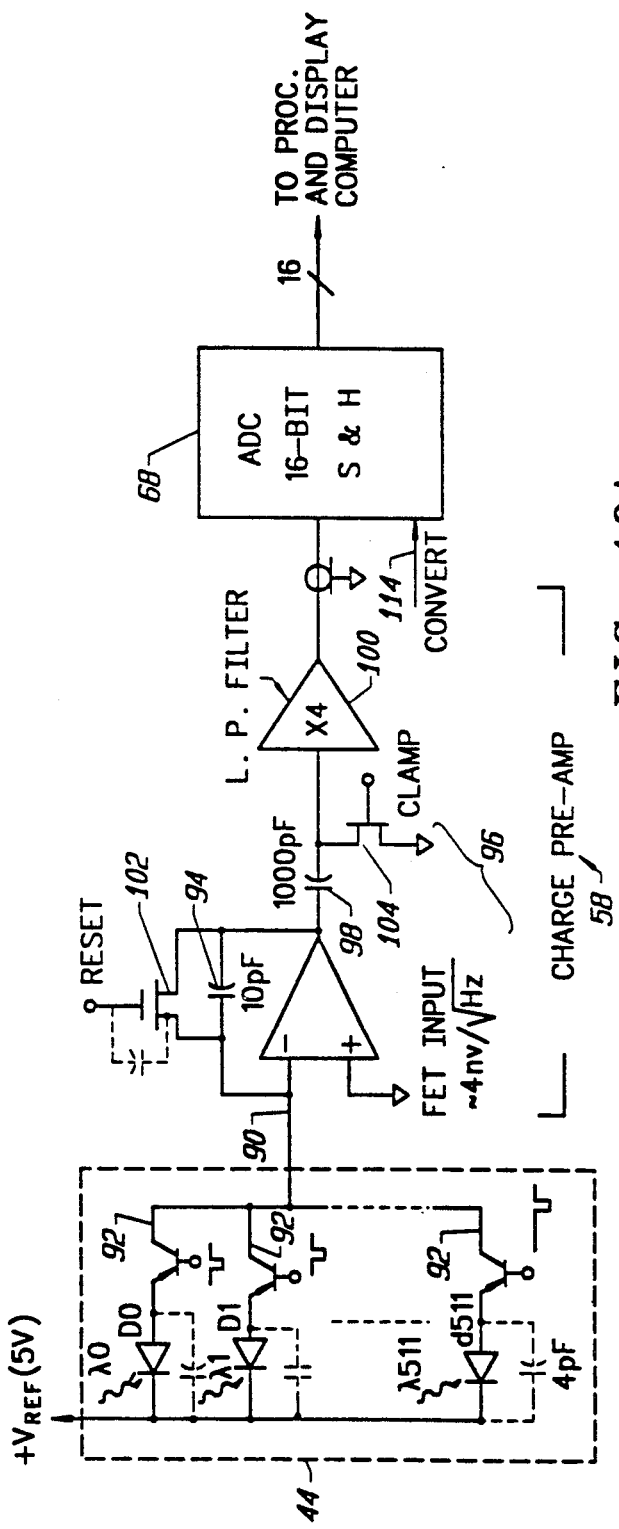
FIG. 10 is a simplified schematic of the photodiode linear array, preamplifier, and ADC of the present invention.
Figure 10B:
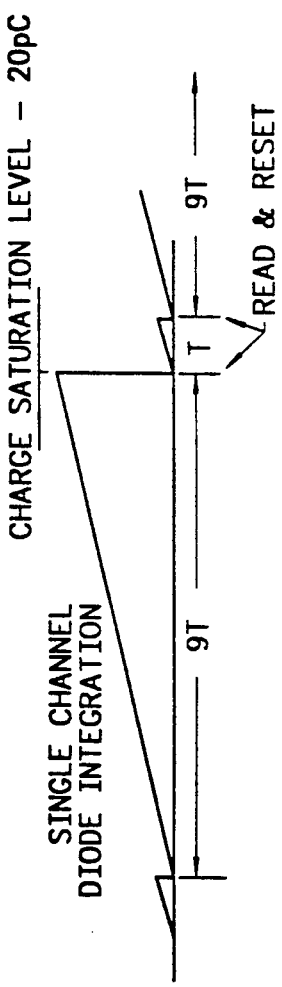
Figure 11A:
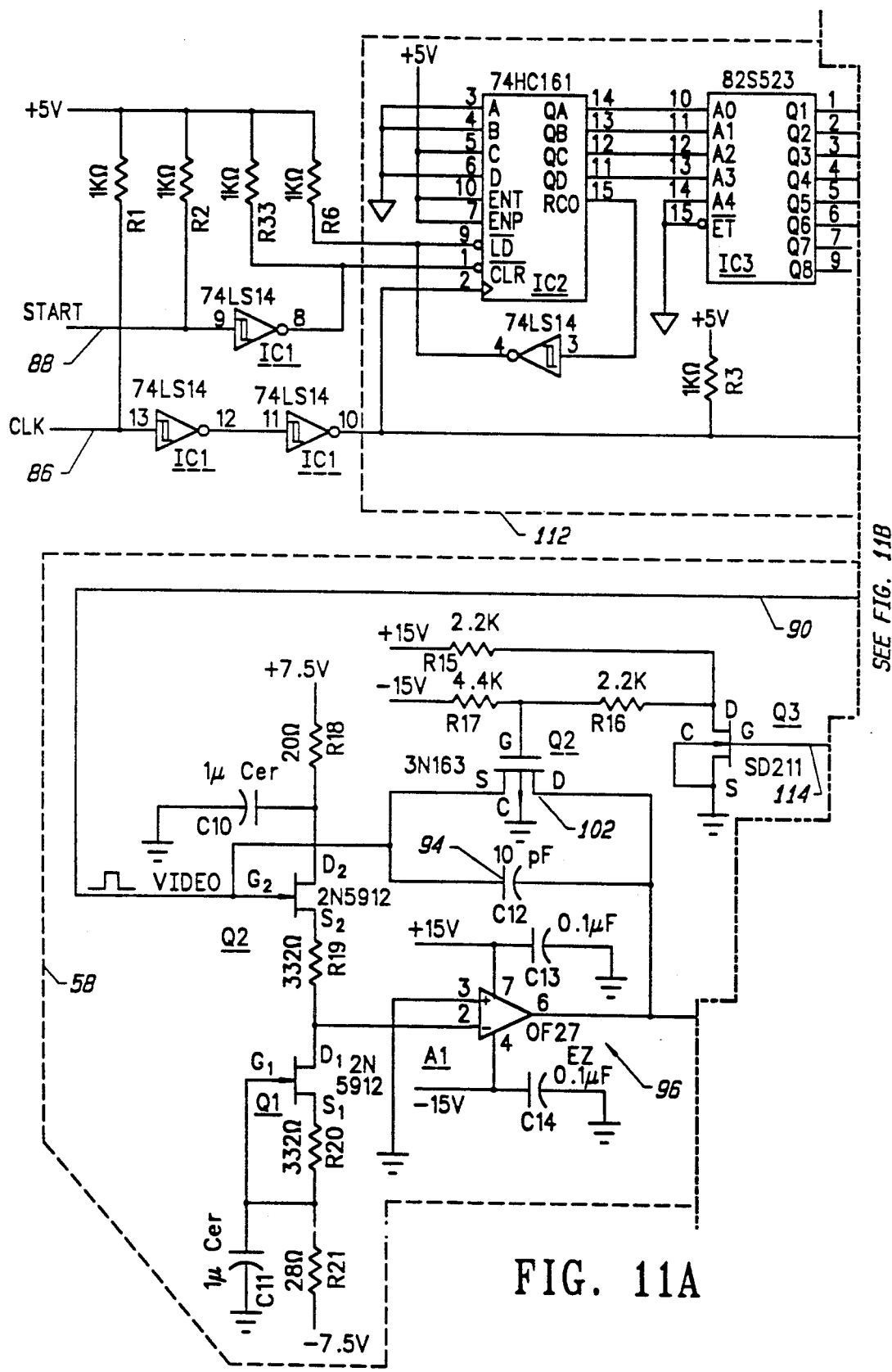
FIG. 11 (which consists of FIGS. 11A, 11B, and 11C) provides a detailed schematic of the circuitry used to implement one embodiment of the pre-amp, integrator, reset and clamp circuit.
Figure 11B:
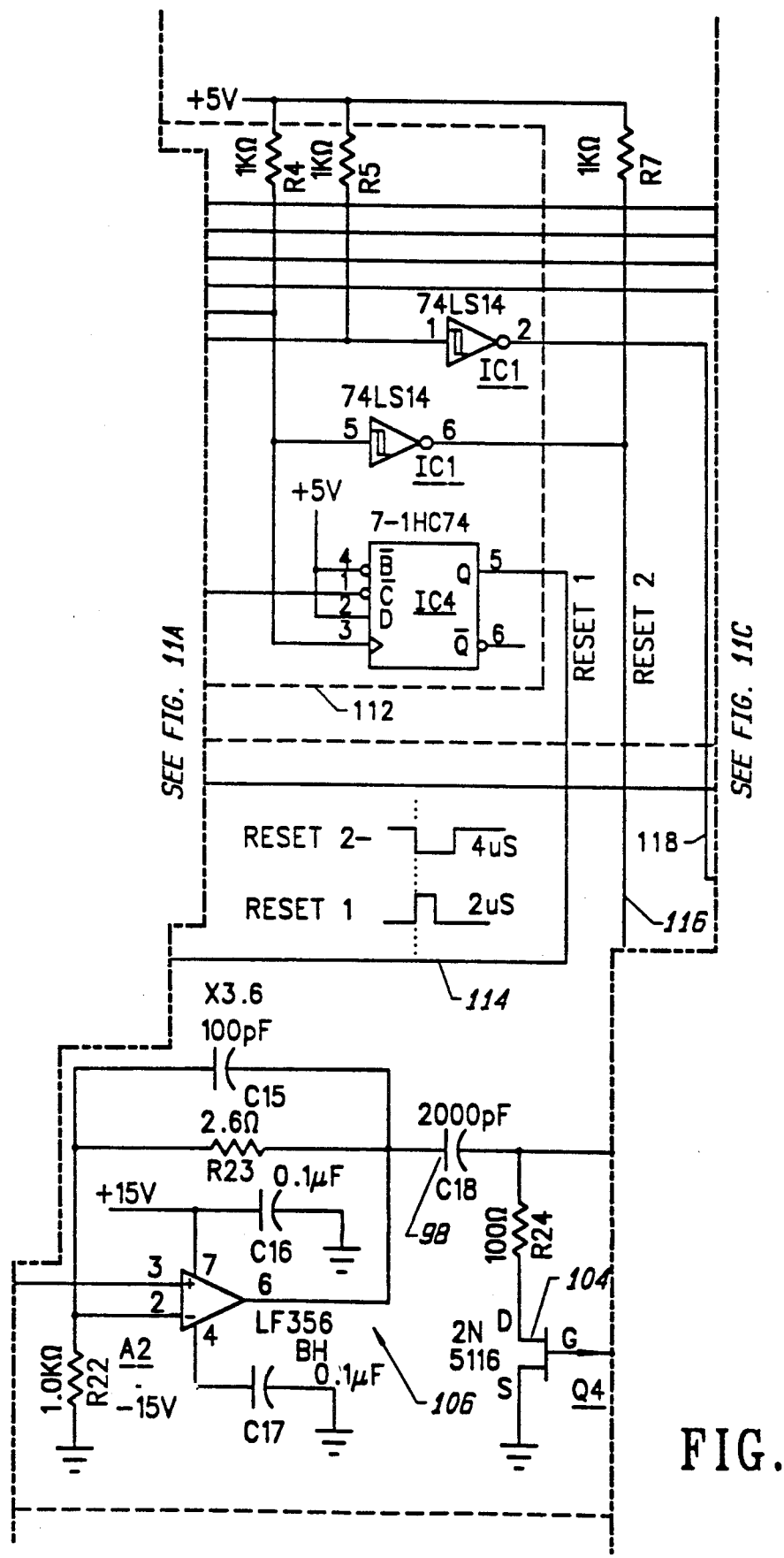
Figure 11C:
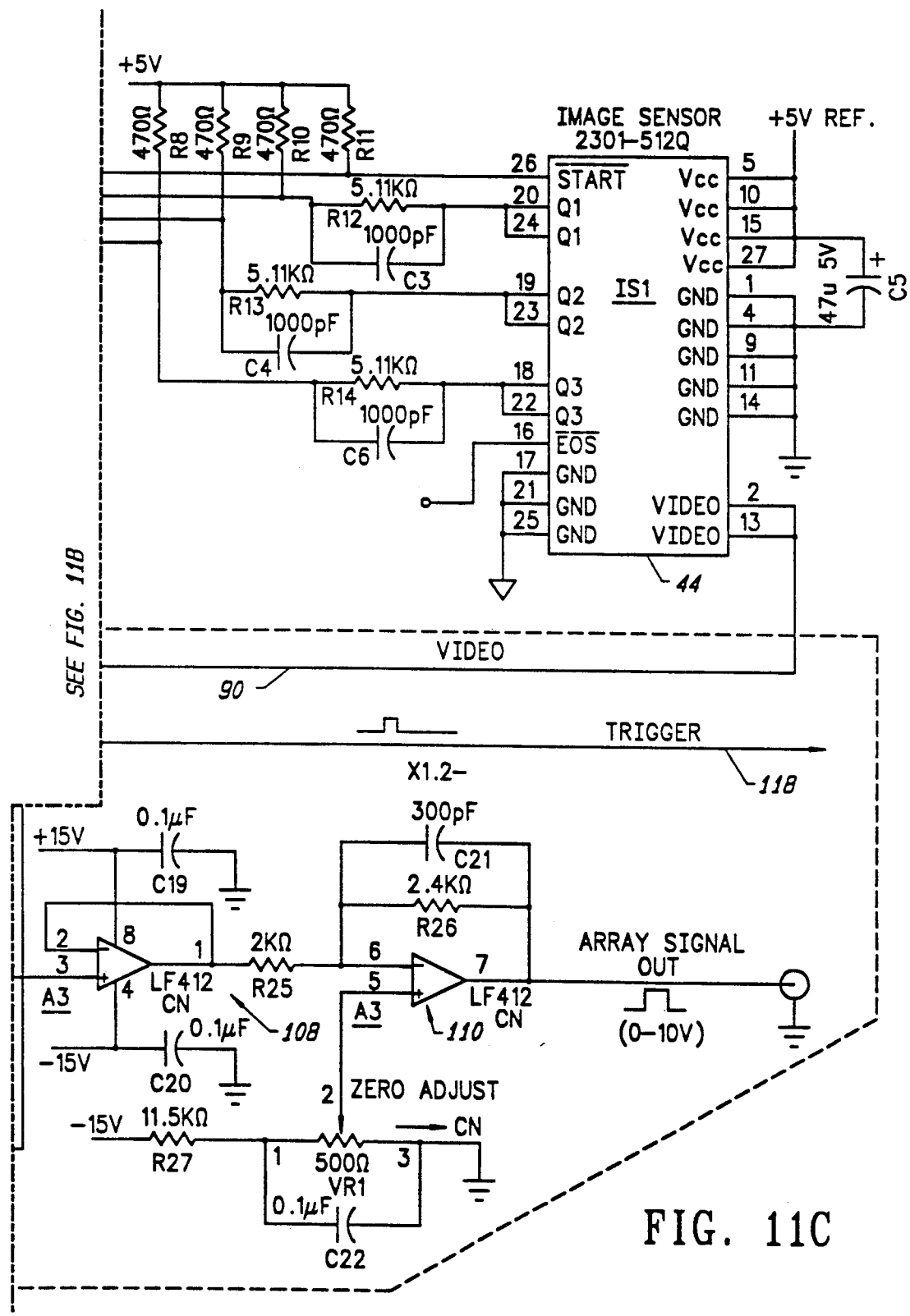

Referring now to FIGS. 10 and 11, the pre-amp, integrator, reset and clamp circuit 58 will be described in greater detail. In FIG. 10, a simplified schematic of photodiode linear array 44 is shown. The anodes of the 512 photodiodes are connected to a low noise reference, such as a bandgap voltage reference. The cathode of each of the 512 diodes is coupled to a video line 90 by way of pass transistors 92. The pass transistors are sequentially pulsed by an internal clock which operates off of sample clock 86, FIGS. 1 and 11.

When a pass transistor 92 is pulsed, the charge which has accumulated on its associated photodiode is placed on video line 90. This charge is transferred onto capacitor 94 which is in the feedback loop of the input stage 96 of pre-amp, integrator, reset and clamp circuit 58. Input stage 96 operates as a charge amplifier and integrator, and provides at its output a voltage proportional to the amount of charge present on capacitor 94. Capacitor 98 couples the voltage at the output of input stage 96 to low pass filter 100, which provides a gain of approximately four. Low pass filter 100 has a high impedance input and acts as a prefilter prior to analog to digital conversion by ADC 68. ADC 68 is a single 16-bit linear analog-to-digital converter.

Input stage 96 includes a low noise, high input-impedance amplifier stage. In the preferred embodiment, a pair of discrete low noise field effect transistors, such as type 2N5912, are used as a front end voltage follower of the amplifier. See FIG. 11. The output of the stacked pair is then applied to the inverting input of a high impedance operational amplifier, such as device number OP-27, manufactured by PMI of Santa Clara, Calif.

Reset and Clamping

The pre-amp, integrator, reset and clamp circuit 58 includes a reset transistor 102 connected in parallel with capacitor 94, and a clamp transistor 104 connected to the end of coupling capacitor 98 connected to low pass filter 100. Reset transistor 102 is pulsed to discharge capacitor 94 in preparation for receipt of charge from the next photodiode being sampled.

It has been found that a random offset voltage is coupled into the signal path by way of capacitive feedthrough from the gate of reset transistor 102. This offset can be on the order of one-half the control voltage being applied to the gate of reset transistor 102. It has also been found that the addition of clamp transistor 104 reduces the above offset by a factor of five.

In operation, reset transistor 102 is pulsed with a positive going pulse for a predetermined time, such as two microseconds. At the same time, clamp transistor 104 is pulsed with a negative going pulse, but for a period about twice as long, such as four microseconds. During the time the clamp transistor 104 is pulsed, coupling capacitor 98 charges to the offset voltage. When the negative going pulse is completed, the end of coupling capacitor 98 connected to low pass filter 100 follows the output of input stage 96, which will assume a voltage proportional to the charge being transferred from the next photodiode being sampled in photodiode linear array 44.

FIG. 11 provides a detailed schematic of the circuitry used to implement one embodiment of the pre-amp, integrator, reset and clamp circuit 58. In this embodiment, low pass filter 100 is implemented in three separate stages: 106, 108, and 110, with coupling capacitor 98 and clamping transistor 104 being located between stages 106 and 108. Stage 106 is non-inverting and provides a gain of 3.6 and low pass filter knee at 610 kHz; stage 108 operates as a follower; and stage 110 in inverting and provides a gain of 1.2 and a low pass filter knee at 220 kHz.

Also shown in FIG. 11 are circuits 112 for generating a three-phase clock for use in sampling the photodiode linear array 44; the reset pulse 114 and clamp pulse 116 supplied to reset and clamp transistors, 102 and 104, respectively; and also the convert signal 118 supplied to ADC 68.

Imaging Extension Detector 45

Figure 12:
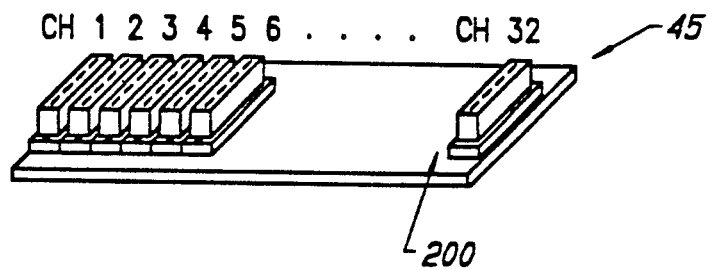
FIG. 12 illustrates the relative positioning of the photodiodes of the imaging extension detector array.
Figure 13:
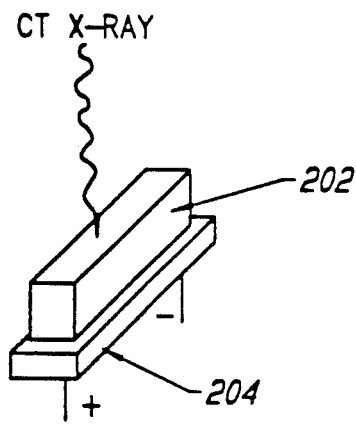
FIG. 13 illustrates a detector from the imaging extension detector array.
Figure 14:
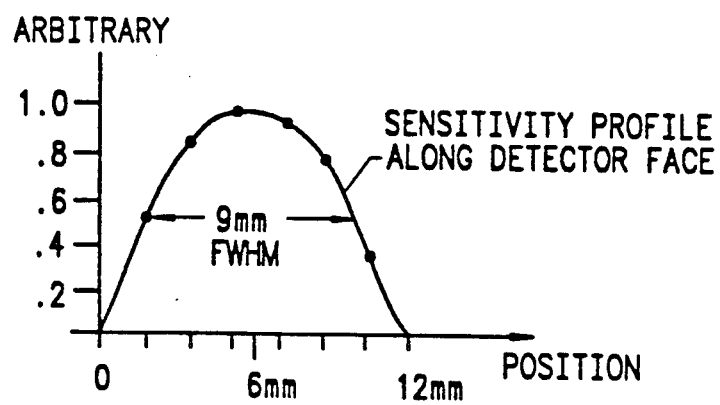
FIG. 14 illustrates the sensitivity profile along the detector face of a detector from imaging extension detector array.

Referring to FIGS. 12, 13 and 14, the imaging extension detector 45 includes an array of 32 discrete detectors 200. Each detector 200 includes a high density cadmium tungstate ($CdWO_4$) scintillating crystal 202 mounted and optically coupled to a UV-enhanced silicon photodiode 204. The scintillating crystals 202 are 2 mm wide by 12 mm long by 3 mm deep, and have the following characteristics:

| | |
|---|---|
| Stopping power of 150 keV gammas in 3 mm | 90% |
| Stopping power of 3 MeV gammas in 12 mm | 30% |
| Light output relative to NaI (Tl) | 40% |
| Wavelength of maximum emission | 540 nm |
| Decay constant | 5 μsec |
| Afterglow at 3 msec | 0.1% |
| Index of refraction at 540 nm | 2.2-2.3 |
| Temp. coeff. of light out at 300 K. | 0%/deg. K. |
| Density | 7.9 g/cc |
| Melting point | 1598 K. |
| Hygroscopic | No |

These crystals are available from NKK of Tokyo, Japan and Harshaw Chemical, of Solon, Oh. Each crystal is resin mounted to a photodiode 204, with the side facing the photodiode being polished, painted with a white reflective coating, and sealed with black epoxy. The photodiodes 204 are preferably model no. S1337-16Br manufactured by Hamamatsu of Hamamatsu City, Japan, and have the following characteristics at 25 degrees C.:

| | |
|---|---|
| Quantum efficiency at 540 nm | 70% |
| Radiant sensitivity at 540 nm | 0.35 A/W |
| Noise equivalent power | $6 \times 10^{-15}$ W/root Hz |
| Rise time | 0.2 μsec |
| Dynamic range | $10^{-12}$ to $10^{-4}$ A |
| Dark current at 10 mV rev. bias | 25 pA max. |
| Junc. cap. at 10 mV rev. bias | 65 pF |
| Dark current at 5 V rev. bias | 60 pA typ. |
| Junc. cap. at 5 V rev. bias | 22 pF |

The photodiodes 204 have an active area of 1.1 by 5.9 mm. The photodiode 204 case of 2.7 mm wide by 15 mm long. This yields detector spacing of 2.85 and the 9 mm length of the imaging extension detector array 45. Each scintillating crystal 202 has an active face of 2 mm by 12 mm, which yields a slice thickness of the imaging extension detector array 45, referred to the isocenter, of 8 mm.

The limitation on photodetector length is due to the photodiode's active length and case size. The x-ray signal is typically very high at the periphery of the scan circle and thus the loss in signal is insignificant. More specifically, the dynamic range requirements at the periphery of the scan circle are a factor of 10 less as compared to detectors at the center. Detectors at the center typically receive the fewest x-ray photons. Further, the width of the imaging extension detector 45, referred to the isocenter, is approximately 1.9 mm, compared to 0.37 mm for the photodiode linear array 44. This yields a spacial resolution approximately a factor of 5 less than the photodiode linear array 44. However, this lower spacial resolution is not significant because high spacial content objects are typically not viewed at the periphery of a body scan circle.

The array is mounted at the edge of the existing 30 cm image intensifier tube face 24. A measured x-ray sensitivity profile along the detector face is shown in FIG. 14. The combination of image intensifier tube 40 and imaging extension detectors 45 forms an overlapping hybrid detector design.

X-ray photons, which have passed through the object being scanned, are incident on the 2 mm by 12 mm face of the scintillating crystals 202. Each photodiode 204 is operated in the photoconductive mode with 5 volts of reverse bias applied after each integration and readout. X-rays absorbed in the scintillator produce light photons which are converted to electron-hole pairs in the diode. The resulting current flow discharges the diode and the preamplifier measures this loss in charge for each channel. This scheme is a discrete circuit implementation that is similar to the approach used in large integrated circuit linear and 2-D photodiode arrays.

Figure 15A:
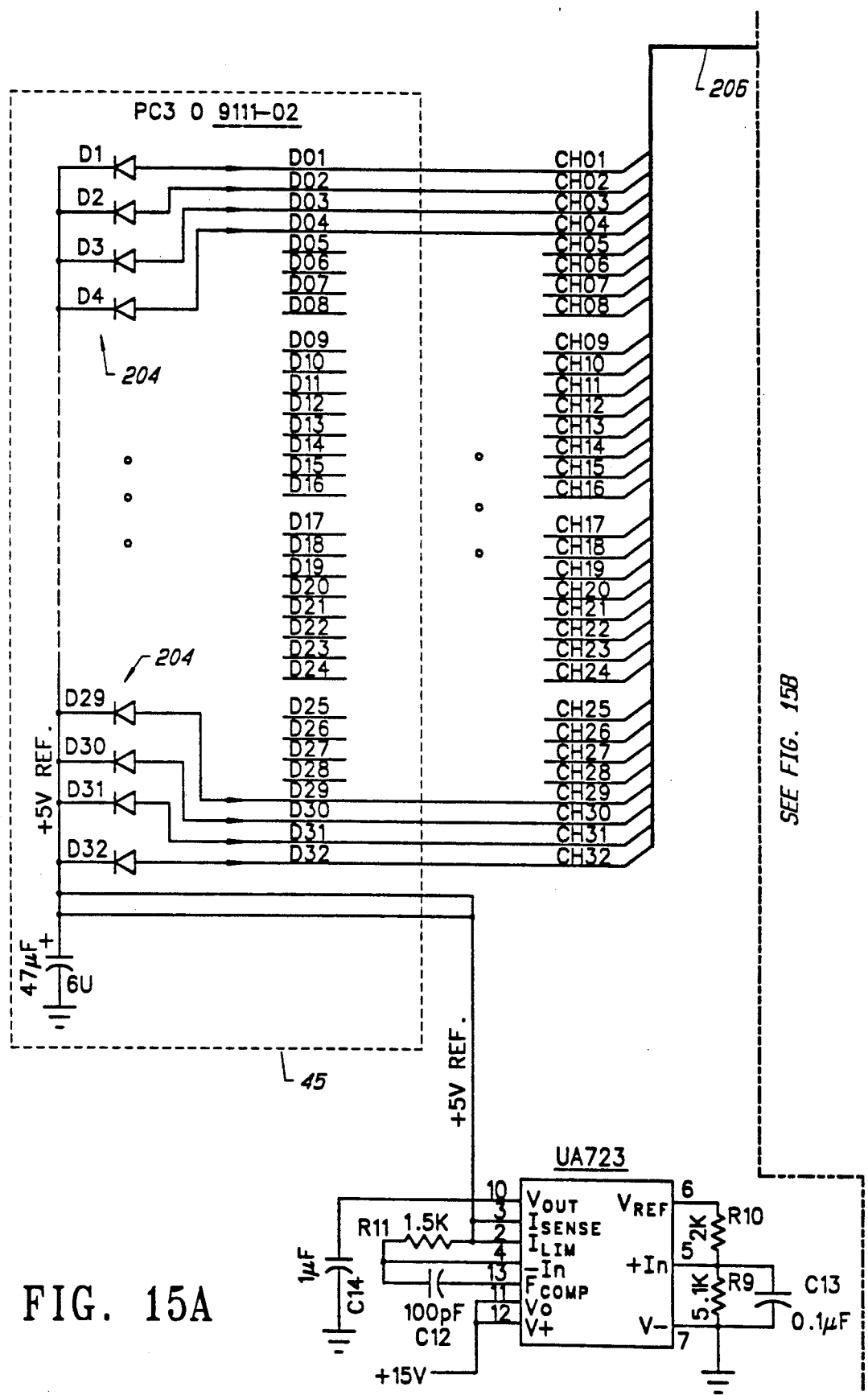
FIG. 15 (which consists of FIGS. 15A, 15B, and 15C) is a detailed schematic of the sampling preamplifier circuitry used with the imaging extension detector array.
Figure 15B:
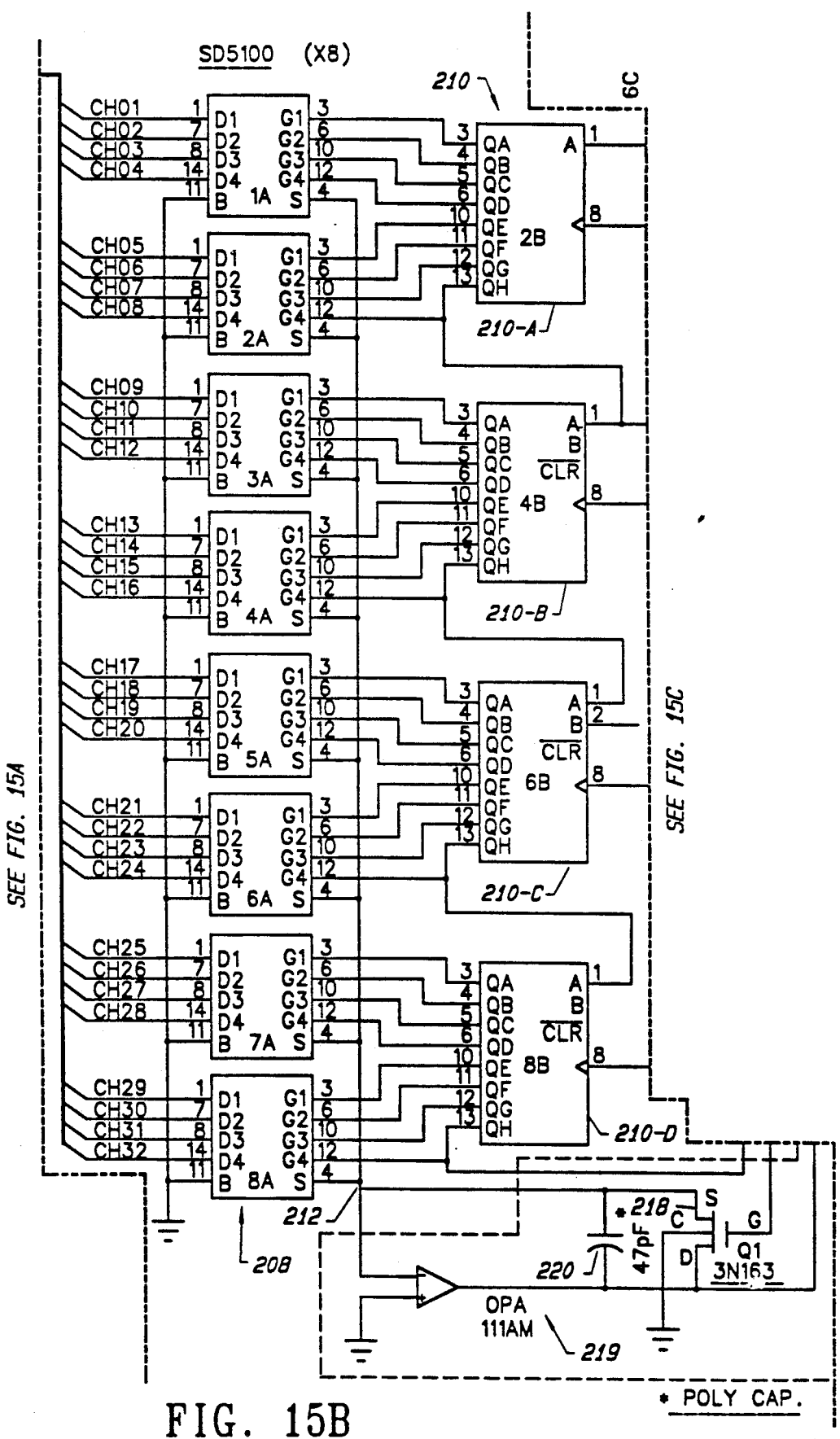
Figure 15C:
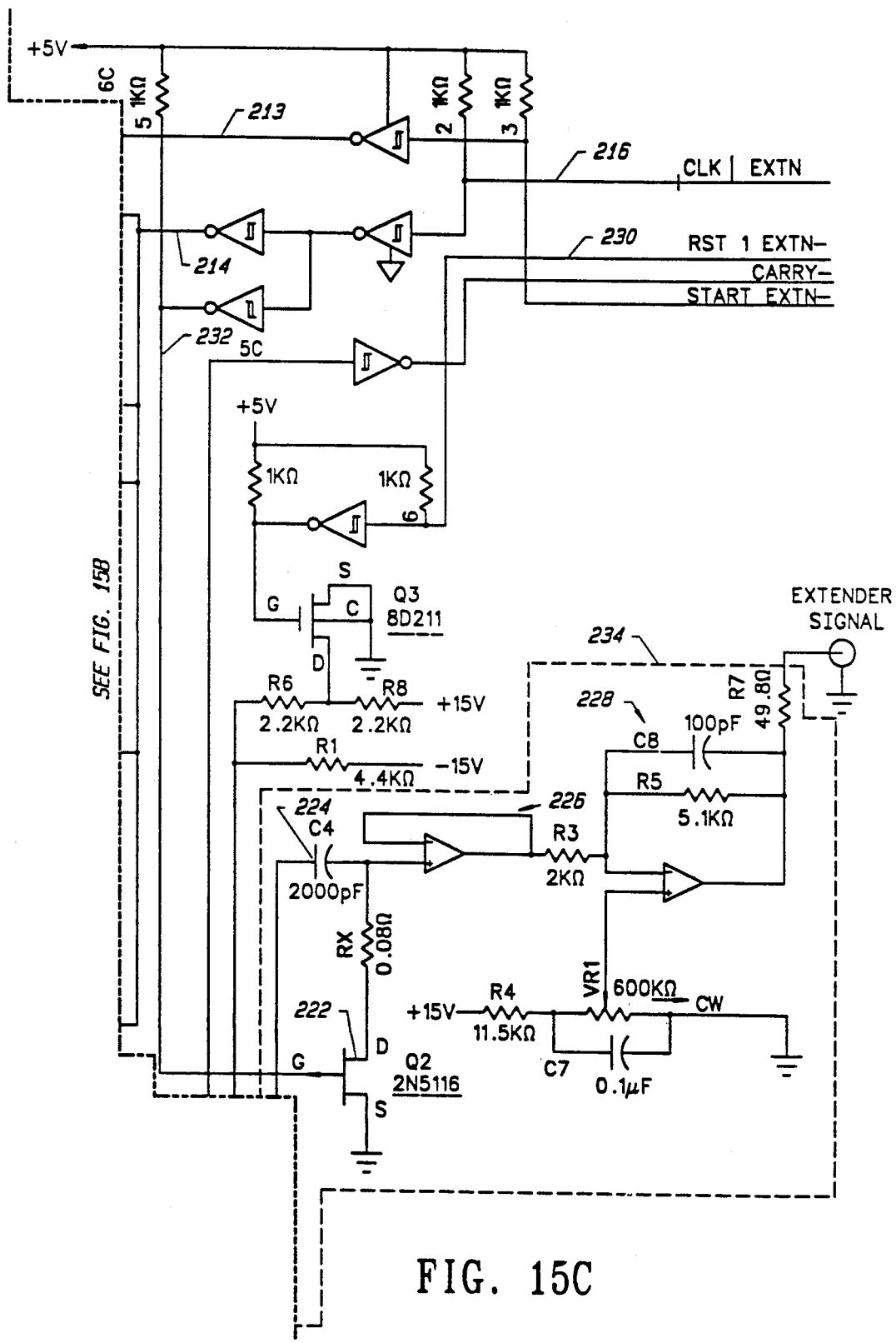

A multichannel scanning charge preamplifier is used to sample each of the 32 detectors and multiplex this data with the existing IIT camera 512 channel data. The sampling of these detectors operate similarly to that used in connection with photodiode linear array 44, described hereinabove. Referring to FIGS. 1 and 15, a simplified block diagram and a detailed schematic of such a circuit are provided.

Imaging extension detector array 45 is connected to pre-amp, integrator, reset and clamp circuit 58 by way of a multiwire harness 206. Signals from each of the photodiodes 204 in the imaging extension detector array 45 are brought out from, and a 5 V reference and ground connections are provided to, imaging extension detector array 45 over the multiwire harness 206. As was the case with the photodiodes of the photodiode linear array 44, a low noise reference is used at the anode of photodiodes 204. The signals from the photodiodes 204 are then applied in parallel to a bank of select circuits 208. These select circuits 208 are controlled by select logic circuit 210 to sequentially and serially place the signals from the photodiodes 204 onto a video line 212.

In FIG. 15, it can be seen that select circuits 208 are gating circuits which transfer data applied at their "D" inputs to the "S" output, under control of signals applied to the "G" terminals. Select logic circuit 210 includes a bank of parallel to serial shift registers 210-A, 210-B, 210-C and 210-D, which operate to scan the bank of select circuits 208. Select logic circuit 210 can be implemented using part number 74HC164.

The scan is begun upon receipt of a start extension pulse on line 213. This pulse is clocked along the parallel to serial shift registers 210-A through 210-D, at a rate set by the extension clock supplied on line 214. As can be seen from FIG. 1, the start extension pulse and extension clock are supplied from control logic 60 on line 216.

As was the case with the photodiode linear array 44, the preamplifier 234 for the imaging extension detector array 45 uses a input amplifier 219 with a capacitor 220 connected in a negative feedback configuration. Line 212 is tied to one end of capacitor 220. A reset transistor 218 connected in parallel with a capacitor 220 to reset it in preparation for receipt of the next sample. A coupling capacitor 224 couples the output of input amplifier 219 to non-inverting amplifier 226. A clamp transistor 222 is connected to the end of coupling capacitor 224 that is connected to non-inverting amplifier 226. Finally, the output of non-inverting amplifier 226 is connected to lowpass filter 228.

Reset transistor 218 is pulsed to discharge capacitor 94 in preparation for receipt of charge from the next photodiode being sampled, and clamping transistor 224 is pulsed during this operation, as is the case with reset transistor 102 and clamping transistor 104 in the charge amplifier for the photodiode linear array 44. The reset pulse for reset transistor 218 is provided on line 230, while the clamping pulse is supplied on line 232 from the extension clock 216.

Data Acquisition Timing and Dual Exposure Time Scheme

Figure 16:
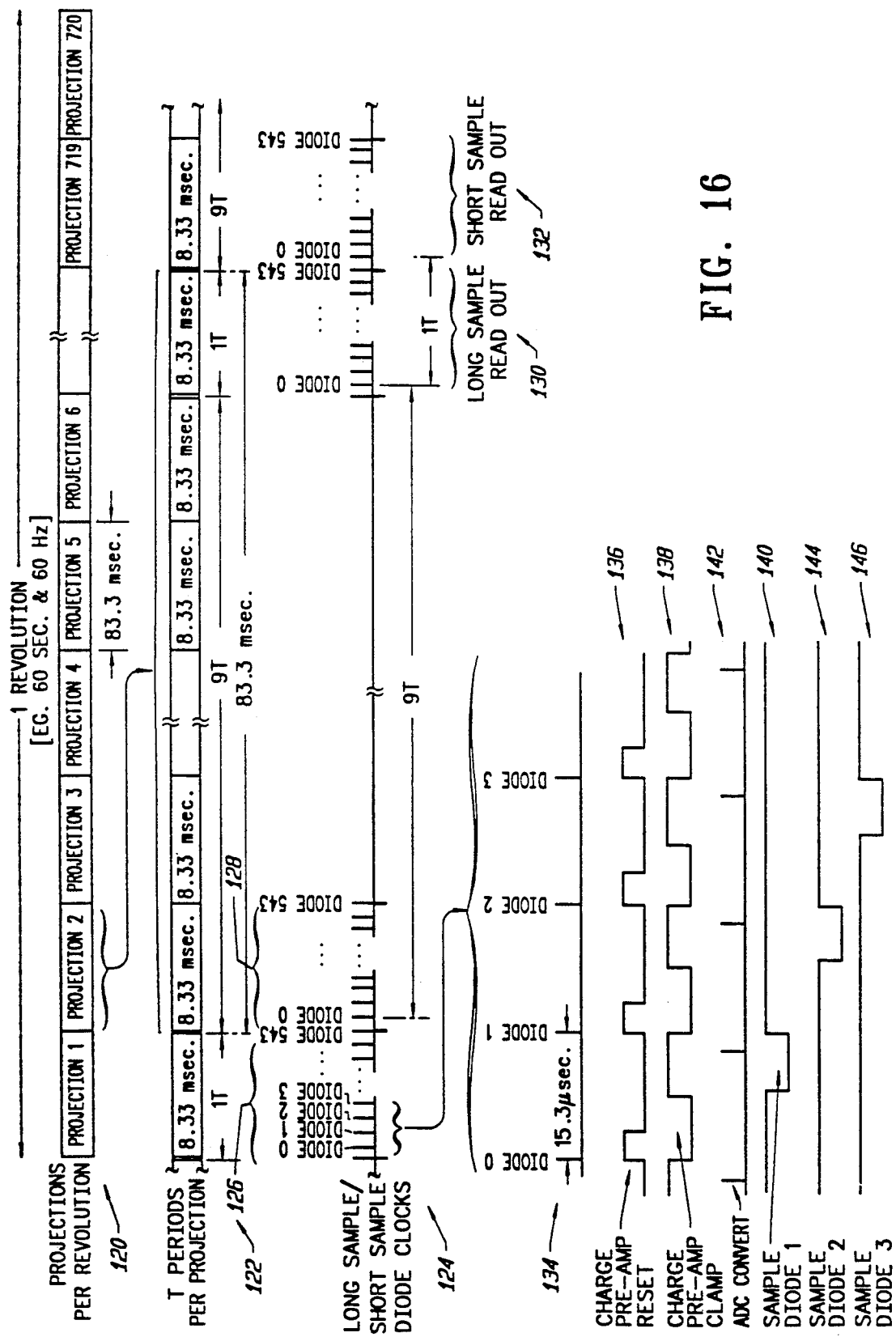
FIG. 16 illustrates the relative timing involved in the data acquisition from the photodiode linear array and the imaging extension detector array.

Referring now to FIG. 16 the relative timing involved in the data acquisition will be described in greater detail. A complete set of X-ray transmission data is obtained by collecting 720 projections or 2 per degree of rotation for 60 seconds. In practice, slightly more projections are collected or slightly more than 360 degrees of rotation. However for purposes of this discussion, 720 projections and 360 degrees of rotation will be assumed.

In FIG. 16, line 120 illustrates the allocation of the 720 projections across one revolution of the X-ray head assembly 18 and image intensifier tube assembly 20 about the object of interest. Each such projection takes up approximately 83.3 msec (60 Hz). Line 122 illustrates how each projection can be view as a series of periods of duration T. The example illustrated in FIG. 16 uses T equal to 8.33 msec. Within a projection, the periods are grouped to define a long sample interval, 9T in length, and a short sample interval, 1T in length.

It has been found that the dynamic range of the photodiode linear array 44 can be greatly increased by utilizing a dual exposure time scheme in the above manner. That is, by using a short sample interval and a long sample interval over which the photodiodes are permitted to convert photons to electrons, the most accurate measurement of the two can be selected for use.

As discussed briefly above, the point spread response of the IIT 20 indicates a dynamic signal range of at least 100,000:1. One the other hand, the single channel dynamic range of the photodiode linear array 44 has been measured to be 35,000:1 when used with the manufacturer's preamp. As such, the photodiodes alone will saturate under high levels from IIT 40. With a two-interval sampling approach, the short interval sample will be the most accurate for high intensity levels from IIT 40, and the long interval sample will be the most accurate for low intensity levels from the IIT 40. This effectively extends the dynamic range of the photodiodes into the 100,000:1 range.

In practice, for the commercially available photodiode array identified hereinabove, the saturation level is 22 picocoulombs. The f-stop of second lens 54 is set so that the photodiodes will not saturate over a short interval period when there is no object in the x-ray beam; i.e. with the beam at 125kVp and 15 mA. Preferably, this f-stop setting will result in a light level at the photodiode linear array 44 of about one-half to three-fourths the saturation level with no object in the x-ray beam.

Returning now to FIG. 16, the timing for the long and short interval sampling will be discussed in greater detail. Line 124 illustrates the points at which the photodiodes of photodiode linear array 44 are sampled relative to one another. In the left-most part of line 124 there is shown a first series 126 of 544 sample points: 512 for the photodiode linear array 44, and 32 for the imaging extension detector array 45. These occur during the left most T-period of line 122; i.e. during the last T-period of projection 1, line 120. In line 124, the second series 128 of 544 sample points occurs during the first T-period in projection 2, line 122. It is to be noted that no sample points occur in line 124 until the ninth T-period of projection 2, line 122. Thereafter, a third series 130 of 544 sample points are shown occurring during the ninth T-period. Finally, a fourth series 132 of 544 sample points are shown occurring during the first T-period of projection 3.

The long interval sample for projection 2 is taken during the third series 130 of 544 sample points. The short interval sample for projection 2.

is taken during the fourth series 132 of 544 sample points. For example, it can be seen from line 124 that the time period between the sampling of diode 1 in second series 128 and third series 130 is nine T-periods. Diode 1 is therefore permitted to integrate the incident photons for nine T-periods before it is again sampled. The samples taken in third series 130 thus represent the long interval sample for projection 2.

Conversely, the time period between the sampling of diode 1 in third series 130 and in fourth series 132 is only one T-period long. Thus, samples taken in the fourth series 132 represent the short interval sample for projection 2.

Line 134 in FIG. 16 illustrates the time for the sample points for diodes 1-4 in series 126, line 124. As can be seen, the time between sample points is approximately 15.3 microseconds. Within this 15.3 microsecond period, the input stage 96 of pre-amp, integrator, reset and clamp circuit 58 is reset (line 136), the clamp transistor 104 is pulsed (line 138), charge from the photodiode being sampled (for example photodiode 1) is placed o the video line 90 (line 140), and convert signal 114 is sent to ADC 68 (line 142). Lines 144 and 146 show the relative timing of the sampling pulses for photodiodes 2 and 3.

It is to be noted that there are four base-clock periods in each diode sample period. These base-clock periods are related to the 262KHz clock 86 from phase locked loop timing and control circuit 62, FIG. 1. Similarly, the 8.33 microsecond duration of each T-period is related to the 120 Hz clock 88 from phase locked loop timing and control circuit 62. Finally, the 13.3 Hz clock 88 from phase locked loop timing and control circuit 62 relates to the duration of nine T-periods.

X-ray Normalization Detector 66

As was discussed hereinabove, the intensity of the x-ray source is monitored by x-ray normalization detector 66, FIG. 1. The signal from x-ray normalization detector 66 is amplified and filtered and then applied to a multiplexer 65. Also applied to the inputs of multiplexer 65 is the signal from pre-amp, integrator, reset and clamp circuit 58. The output of multiplexer 65 is then applied to ADC 68. A select signal 61 is supplied from control logic circuit 60 to select between the signal from x-ray normalization detector 66 or the from pre-amp, integrator, reset and clamp circuit 58 for conversion by the pre-amp, integrator, reset and clamp circuit 58.

A simple optical switch (not shown) is mounted on the drive stand and a corresponding "finger" is attached to the main gantry gear wheel. This arrangement generates a pulse when the gantry goes through zero degrees, indicating start of scan. The next pulse from the optical switch (360 degrees of rotation later) signals the end of a scan. When the system is ready for data collection, this trigger initiates data acquisition, a pre-set number of projections are always collected, and the end of scan pulse sets a flag in the projection data.

To allow for variations in gantry rotation speed the data collection controller is set to acquire more projections than are required, so there is a slight overscan (5-10 degrees) at the beginning and end of the gantry rotation. This allows the x-ray generator output to settle and the gantry to reach constant angular velocity before data acquisition begins. Data acquisition stops as soon as the end of scan pulse is detected and the x-ray generator can be turned off.

A gantry angle encoder and logic circuit 70 is attached to the potentiometer which measures the angle of the rotating arm 12. This encoder nominally gives ten (10) pulses per degree of gantry rotation and hence allows the determination of projection angles to 0.1 degree (12-bit counter).

Data Acquisition Interface 48

Data acquisition interface 48 is an optically isolated interface which utilizes conventional photodiodes and a receiver link. Use of an optical link greatly reduces electrical ground problems.

In addition to the digital data and handshake signals from ADC 68 and gantry angle encoder and logic circuit 70, an analog channel (not shown) is brought out from amplifier and filter 64 via data acquisition interface 48 for use in calibration and set up purposes.

Processing and Display Computer 50

Processing and display computer 50 is preferably a conventional 80286 based personal computer. A conventional 20 MFlop array processor, a 250 MB WORM (write-once-read-many) optical disk drive, a 4 MB RAM memory, 30 MB hard disk, and an image display card, available from Matrox of Canada, are also used.

DATA CORRECTION, NORMALIZATION AND LINEARIZATION

Further improvements are made possible by correcting the data for certain known error sources. The processing and display computer 50 corrects for detector system spatial and intensity non-linearities and offsets. To minimize the effects of the point spread response of the IIT 40, the data is preprocessed in the processing and display computer 50 by the array processor. That is, after background subtraction and normalization, the array data is convolved with an empirical filter which compensates for the non-ideal point spread response. After all the projection data is obtained, a $512 \times 512$ pixel image is then generated using a convolution and back-projection technique. The resulting CT image has better than 1 mm spatial resolution and 1% density resolution on a 20 cm water calibration phantom.

Sources of Error

Possible sources of error in acquired data lie in both the imaging chain and in the mechanical system. Imaging chain sources of error (in no particular priority order) are: 1) time varying x-ray flux from X-ray source 30; 2) photon scatter; 3) image intensifier tube 40 (non-linearity across face, s-curve distortion, EHT variation with current, center detector, edge effects, curved face, dark current); 4) photodiode linear array 44 (non-linear response, saturation, long versus short integration values, dark current); and 5) optics (internal reflections, distortion, mirror alignment).

Mechanical system sources of error are: 1) wandering isocenter 74; 2) mechanical flexing; 3) non-uniform rotational speed; 4) lack of stiffness in IIT structure; and 5) non-repeatability of machine positioning.

The x-ray flux from the X-ray source 30 can vary with time (power frequency fluctuations, photon statistics, etc.). This is measured directly by means of x-ray normalization detector 66. The output from x-ray normalization detector 66 provides a current proportional to the number of incident photons. It is assumed that this device is perfectly linear and the readings from the other detectors are normalized to it, i.e., detector elements are scaled as if the x-ray flux was constant and at its peak value.

Scatter of x-ray photons during their passage through the body is difficult to correct for. The approach used in the present invention is to attempt to eliminate scatter problems by: 1) accurately collimating the fan beam, and 2) using a 14:1 cylindrically focused scatter suppression grid in front of the face of the IIT, although this does cause loss of primary x-ray photons.

Errors and distortion from the image intensifier tube 40 can arise for the following reasons: 1) uneven distribution of absorbing material/scintillator (CsI) at the face; 2) curvature of the glass face and its increasing thickness away from the center; 3) observed spatial non-linearity across the face of the IIT due to electron focusing errors; 4) s-curve distortion which varies as the IIT 40 is reoriented in the earth's magnetic field; 5) dark current (i.e., noise); 6) dynamic range (max signal:-noise); and 7) finite point spread function across the tube face due to internal optical light scatter at the input and output of the tube.

Distortions and errors in the optical path are generally due to internal reflections and lens imperfections and can be summarized by the system point spread function.

For the system, overall light intensity is not a limitation, but x-ray photons are. The second lens 54 f-stop is generally set to 5.6 so it could easily be opened up to 4.0 to allow twice as many light photons through. The IIT 40 has a QDE of 1,000-10,000, therefore there can be a loss of light photons before the QDE of the system reduces to unity. Potential sources of errors in the detector array are: 1) non-linear detector/amplifier response with respect to number of light photons detected; 2) dark current; 3) different response with changes in integration period (for a given light input); 4) detector saturation; and 5) non-repeatability of center detector position.

Calibration

A calibration procedure has been implemented to quantify and correct for data acquisition errors. The image intensifier tube 40, optics, and photodiode linear array 44 chain are treated as a single unit for the purposes of calibration and data correction. Information obtained as a result of these calibration steps is used to correct the data collected during an actual scan.

The calibrations are performed in the following order: a) mirror alignment; b) dark current (background); c) center detector and detector array limits (fan angle limits); d) detector system spatial linearity; and e) system point spread function. Additionally, every detector array is calibrated for response non-linearities by using a calibrated light source.

Physical Alignment of the System

Figure 17:
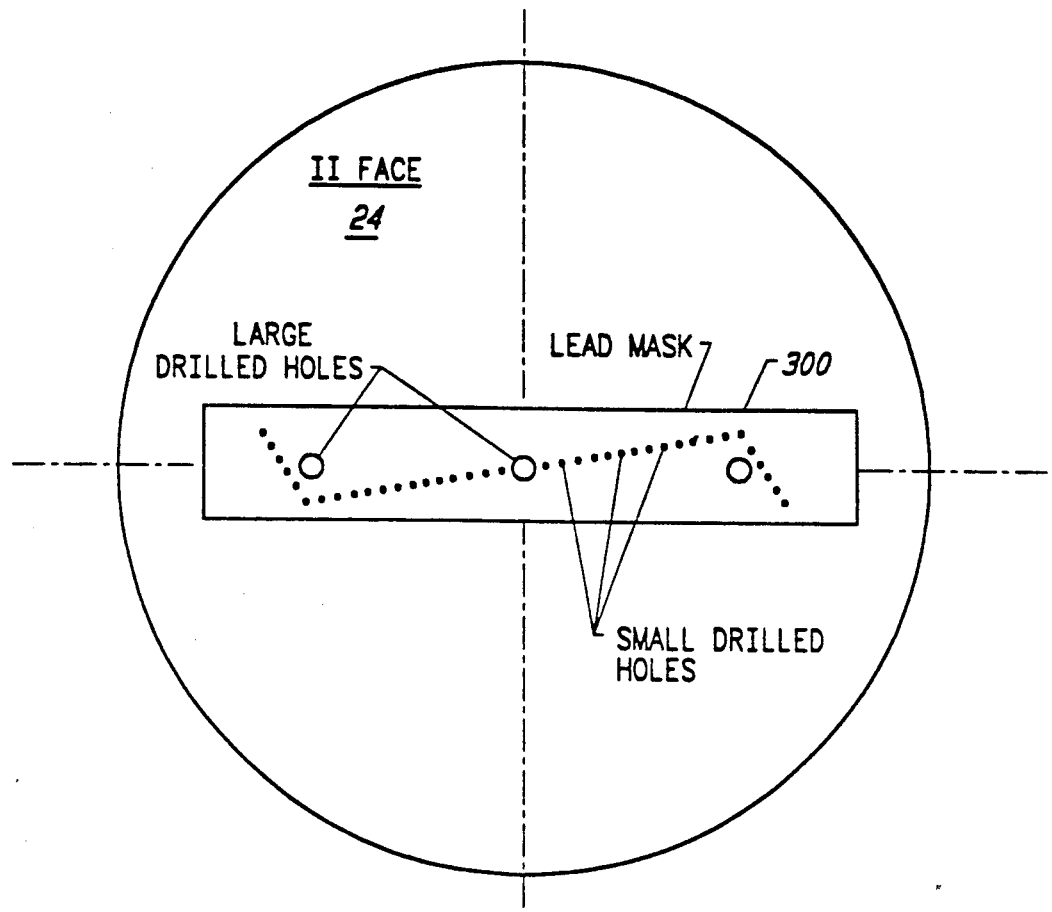
FIG. 17 shows a top view of the mirror alignment apparatus.

Physical alignment of right angle flip mirror 42 in this system is important since a highly collimated beam of light is to be projected onto a long narrow detector array. The adjustment is carried out when the system is installed by carefully centering a specially drilled lead mask 300 over the face of the image intensifier tube 40. See FIG. 17. The incident x-ray beam is collimated so that only the drilled area of the mask 300 is illuminated and the x-ray flux is adjusted so that none of the detectors saturate. The mirror is adjusted so that the response (displayed on an oscilloscope) of the detectors in the photodiode linear array 44 is symmetrical, flat, and with the correct number of detector peaks.

Figure 18:
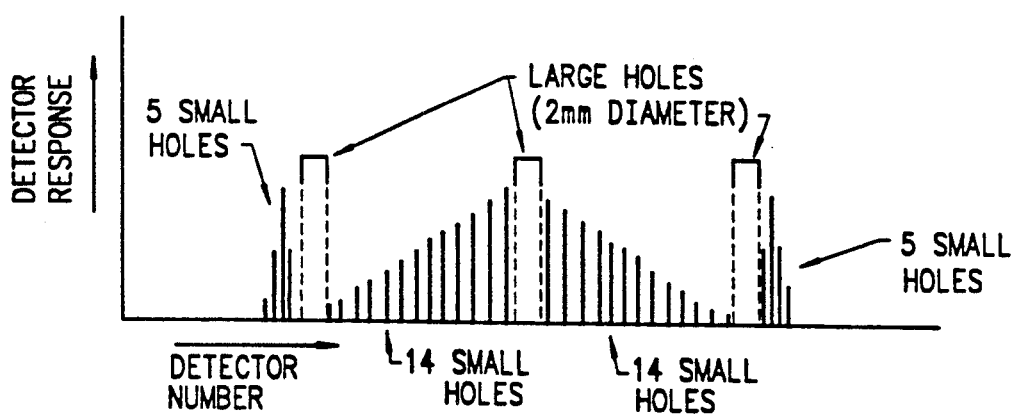
FIG. 18 shows a plot of detector response using the mirror alignment apparatus of FIG. 17.

FIG. 18 illustrates the typical detector response pattern obtained when using the mask 300. As can be seen from the figure, the magnitude of response is greater for the detectors which receive signals from the large drilled holes.

The focus of first lens 52 and second lens 54 may be adjusted by looking at the "sharpness" of the detected peaks. See FIG. 18. This adjustment need not be performed again unless any of the elements in the optical chain are changed.

Background Noise Measurement

The detector system dark current (noise) is determined by collecting data with the x-ray beam off. The usual number of data projections are collected. The readings for each detector are then summed and averaged to give an average dark current (i.e., background) for each individual detector element in the array.

Dark current is a strong function of temperature, therefore calibration values should be taken as a function of temperature, including temperatures during warm-up and room ambient. The averaged background values are stored and subtracted from any data collected when the beam is on.

Identifying Center Detector

Figure 19:
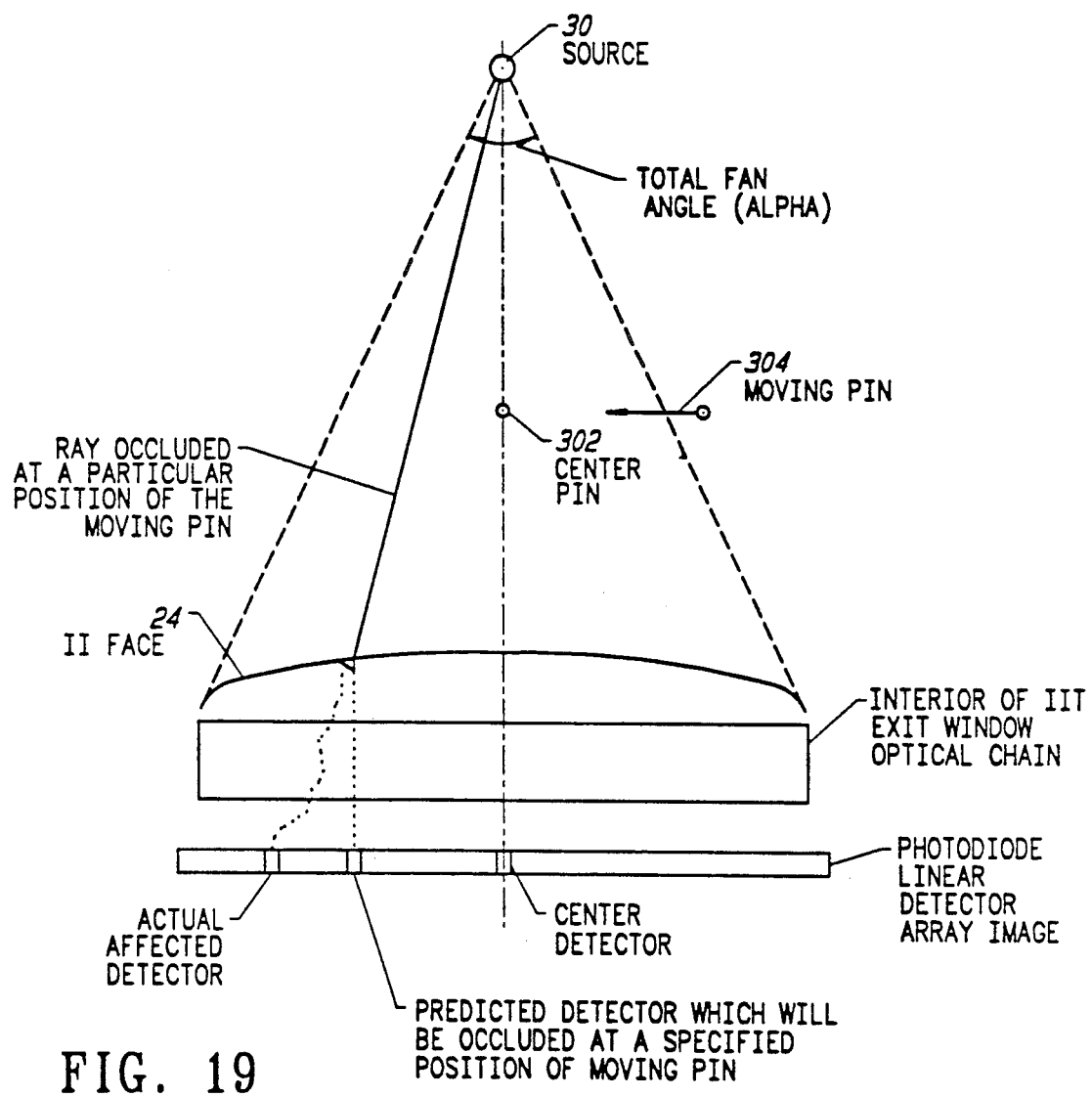
FIG. 19 shows the moving pin arrangement used in the center finding procedure of the present invention.
Figure 20:
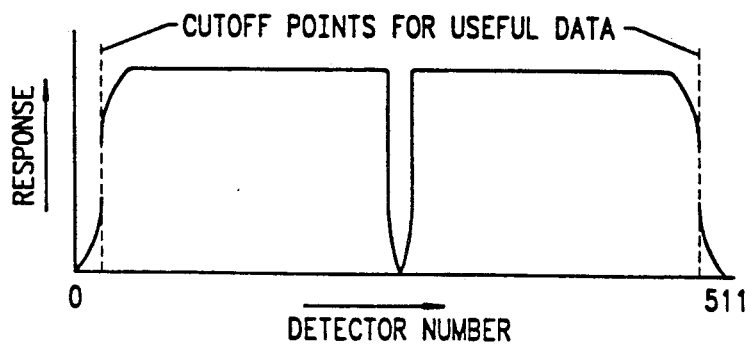
FIG. 20 shows a plot of detector response in the center finding procedure of the present invention.

Referring to FIG. 19, the center detector is identified as follows: 1) collect background data; 2) set the x-ray flux so that no detectors saturate; 3) collect data with nothing in the beam; 4) set a pin or needle 302 at the isocenter 74; 5) ignore detectors close to the ends of the photodiode linear array 44 where readings fall off rapidly; 6) run a scan of the pin to collect a full set of readings. FIG. 20 shows a typical set of readings for any particular projection.

The readings are then processed as follows: a) background correct the data; b) select long/short integration values (the longs will always be selected since the x-ray flux is set so that no detectors saturate); c) calculate ln(air norm)−ln(data); and d) set non-useful detectors to zero.

The results of the calculations are 0 (zero) for most detectors, with a positive the detectors which "saw" the pin 302.

The peak attenuation values for each projection are identified and a corresponding interpolated detector number calculated, i.e., the center detector for that projection.

All the center detector values from each of the projections are then averaged to compensate for the possibility that the pin was not placed exactly at the isocenter 74 and for the flexing of the mechanical structure. The result is the identity of the center detector for the system, which is then saved for future use.

Detector Spatial Non-Linearities

When a ruler with attenuating markers is placed over the face of the IIT and irradiated, the markers will not be equally spaced when viewed at the exit window of the IIT, if there are spatial non-linearities in the detector system. In other words, although the photodetectors in photodiode linear array 44 are uniformly spaced, various effects in the IIT 40 and the imaging path can cause a detector, other than the predicted detector, to be affected when an object is positioned in the fan beam. See FIG. 19.

Among the factors which influence spatial (or geometric) non-linearity are the curvature of image intensifier tube face 24. As can be seen from FIG. 19, the tube face has a convex shape with respect to the fan-beam. This results in rays at the outside of the beam striking the face 24 at a larger relative displacement than rays near the center of the beam. Within the image intensifier tube 40, non-linearities in the focusing grids G1, G2 and G3, can cause the trajectory of emitted electrons to depart from the predicted path. Lens errors in first lens 52 and second lens 54, and mispositioning of the right angle flip mirror 42, are also a source of spatial non-linearities.

In order to determine such system spatial non-linearity a second pin 304 is placed at an offset from the center pin 302 and then moved slowly through the beam. See FIG. 19. In practice, this effect is actually achieved by keeping the pin fixed and rotating the gantry.

Referring to FIGS. 33a through 33c, this effect is illustrated in simplified form. In each of the figures, top dead center (TDC) of the gantry rotation path is shown at the top of the figure. The circle illustrates the path of the gantry rotation. X-ray source 30 is shown in a different position in each of the figures. For these different positions of X-ray source 30 it can be seen that a different detector in photodiode linear array 44 is affected by the occluded ray 306.

The angle $\theta$ indicating the angle between center line 75 and TDC, is measured using gantry angle encoder and logic circuit 70. Angle $\alpha$ is the angular position of the calibration needle 304 from top dead center. The angle $\delta$, can then be calculated from $\theta$, $\alpha$, the distance from X-ray source 30 to isocenter 74, and the distance between isocenter 74 and calibration needle 304, using well known geometric techniques.

From this data the angle of the occluded ray 306, and the detector which responded to the occluded ray 306, can be tabulated. See FIG. 21, where such a table is shown with data selected to illustrate the concept. From the geometry of the system, the detector which should have been affected for any position of the "moving" pin 304 can be predicted. This information is also included in the tabulation of FIG. 21. The total fan angle is calculated by examining when the "moving" pin moves into the fan beam and then leaves it.

In the reconstruction method used in the CT simulation of this example, data corresponding to rays of equal angular displacement are assumed. From the tabulated data, FIG. 21, and corresponding detector readings taken during an actual projection, an intensity reading can be determined for the specific angles desired. The manner in which this information is used in connection with actual measurement data is described in greater detail hereinbelow in connection with FIG. 22.

System Point Spread Correction

Figure 23:
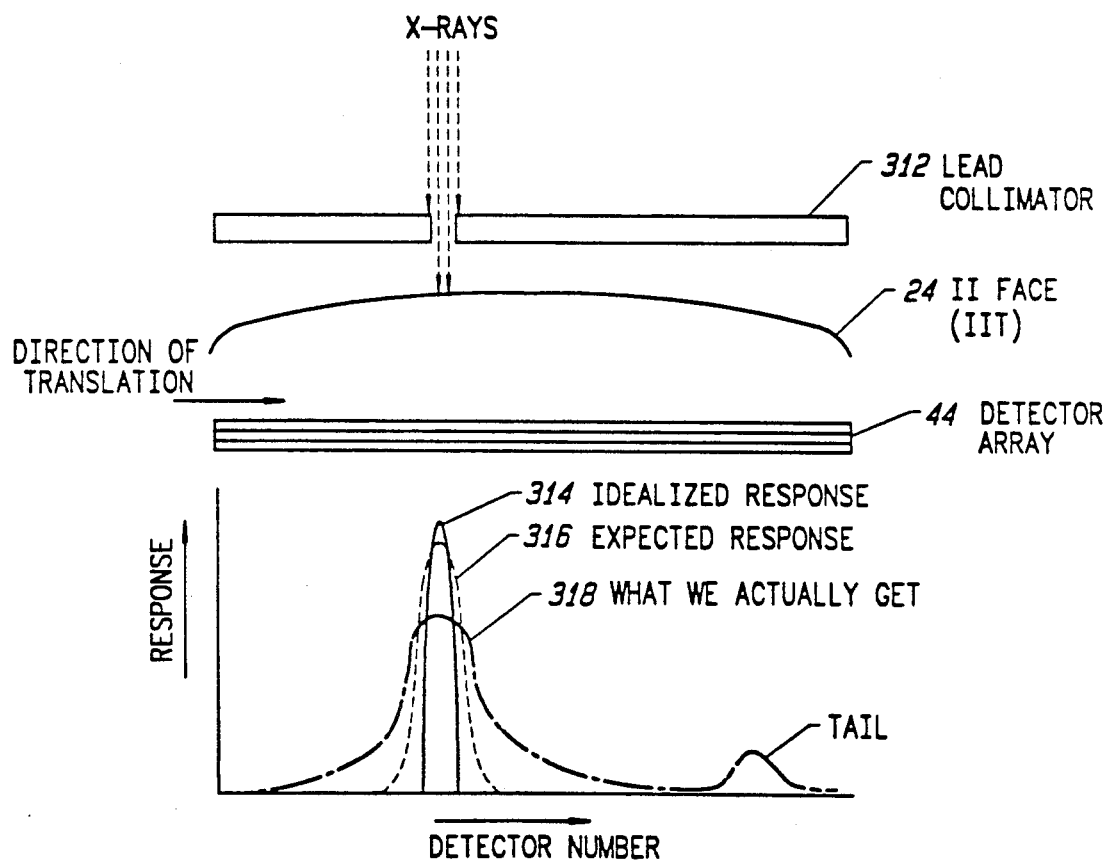
FIG. 23 shows the apparatus and response for determining the point spread function.

The system point spread function (PSF) is an inherent problem in the imaging chain and is due to: 1) defocusing of electrons in the IIT 40, 2) defocusing and scatter of light photons in the optics, and 3) internal reflections within the optics. As illustrated in FIG. 23, the point spread function is measured by using a lead slit 312 in conjunction with post patient collimator 36, to cause a selected spot to be illuminated on image intensifier tube face 24. In the preferred embodiment of the present invention, the PSF is determined by positioning the lead slit at isocenter 74 and collecting data as the IIT 40 is moved laterally by the simulator motor system on arm 16. The IIT 40 is moved to a position where a detector is fully illuminated and the detector array readings for that position are read out. This is repeated until all 512 detectors of the photodiode linear array 44 have been illuminated and readings for the other 511 photodetectors in the array taken.

The idealized response to this excitation is shown as curve 314 at the bottom of FIG. 23 as being all zero except in the immediate vicinity of the photodetector which receives the intensified photons from IIT 40. The dashed line 316 in the figure shows the expected response, taking into account the physical limitations of the imaging system. Finally, curve 318 shows what has been actually measured. It is to be noted that there is a distinct "tail" in the response, located symmetrically opposite the real peak.

There is a different PSF for each slit position over the face of the IIT, and a different tail. The magnitude of these "tails" increases as the slit is moved towards the edge of the IIT 40. This has important implications for body scans using a partial-fan beam. Typically, one side of the IIT 40 is very brightly illuminated by x-rays after passing through the periphery of the body, while the other side is dark because not many x-ray photons manage to get through the center of the body. In this case, the "tails" can be so large as to swamp out valid readings.

From the measured data a deconvolution function is obtained for each slit position (and hence for every detector in the array) which then can be applied to correct the actual detector readings to obtain the idealized response, untainted by the PSF tails. This means that for every fan (i.e. projection) of data, there can be 512 deconvolutions.

Figure 24:
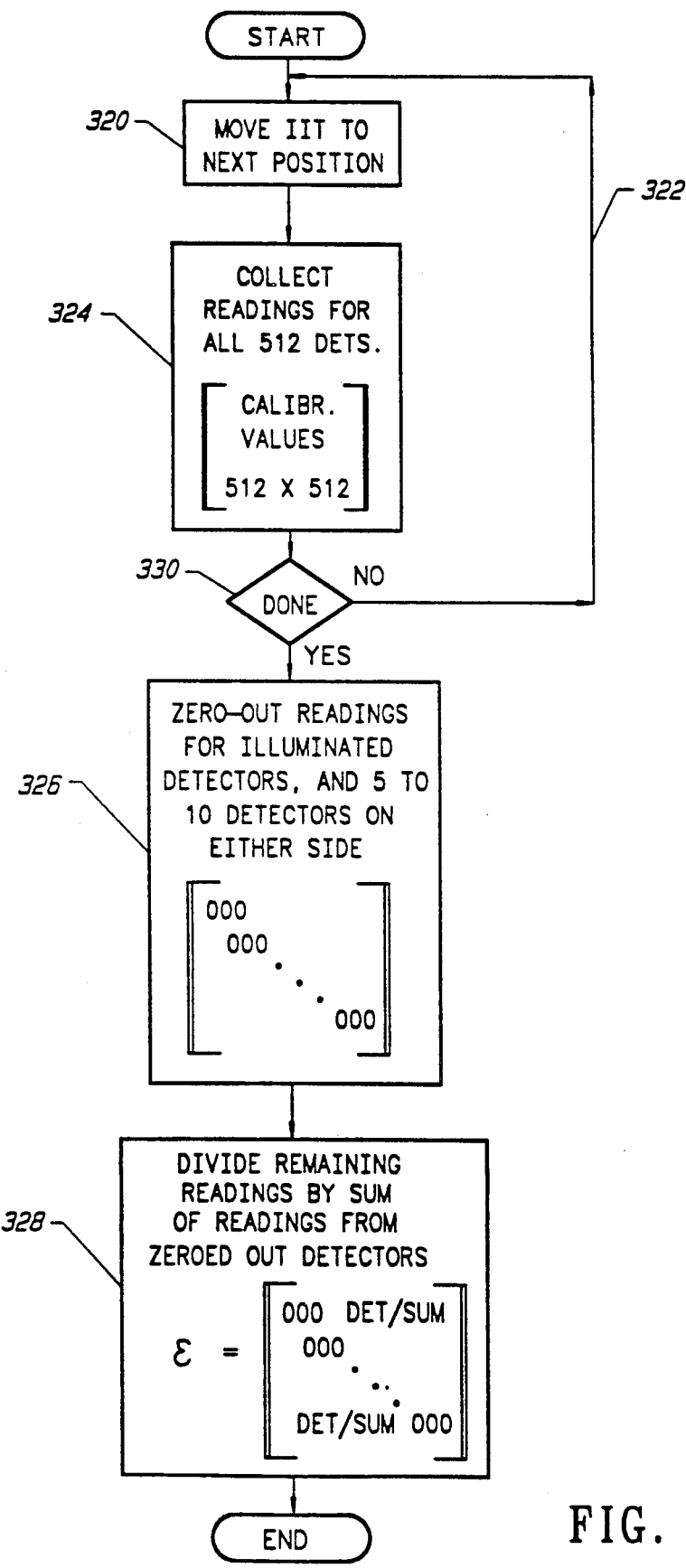
FIG. 24 illustrates the gathering and preparation of the point spread function data.

In practice, these "deconvolutions" are implemented in the following manner. Referring to FIG. 24, the gathering and preparation of the PSF data is illustrated. In step 320 IIT 40 is positioned so that successive photodiodes in photodiode linear array 44 are illuminated as loop 322 is repeated. Once slit 312 has been moved to the next position, readings for all 512 photodetectors are taken and placed into a matrix of calibration values in step 324. Such a matrix might be arranged so that each column corresponds to the detector readings for a particular slit position, and so that each row corresponds to the magnitudes read at particular detector over all of the slit positions.

Step 330 checks to determine if all slit positions have been interrogated. If no, loop 322 is repeated and the slit 312 is "moved" to the next position. If yes, the PSF data gathering is completed.

Figure 25:
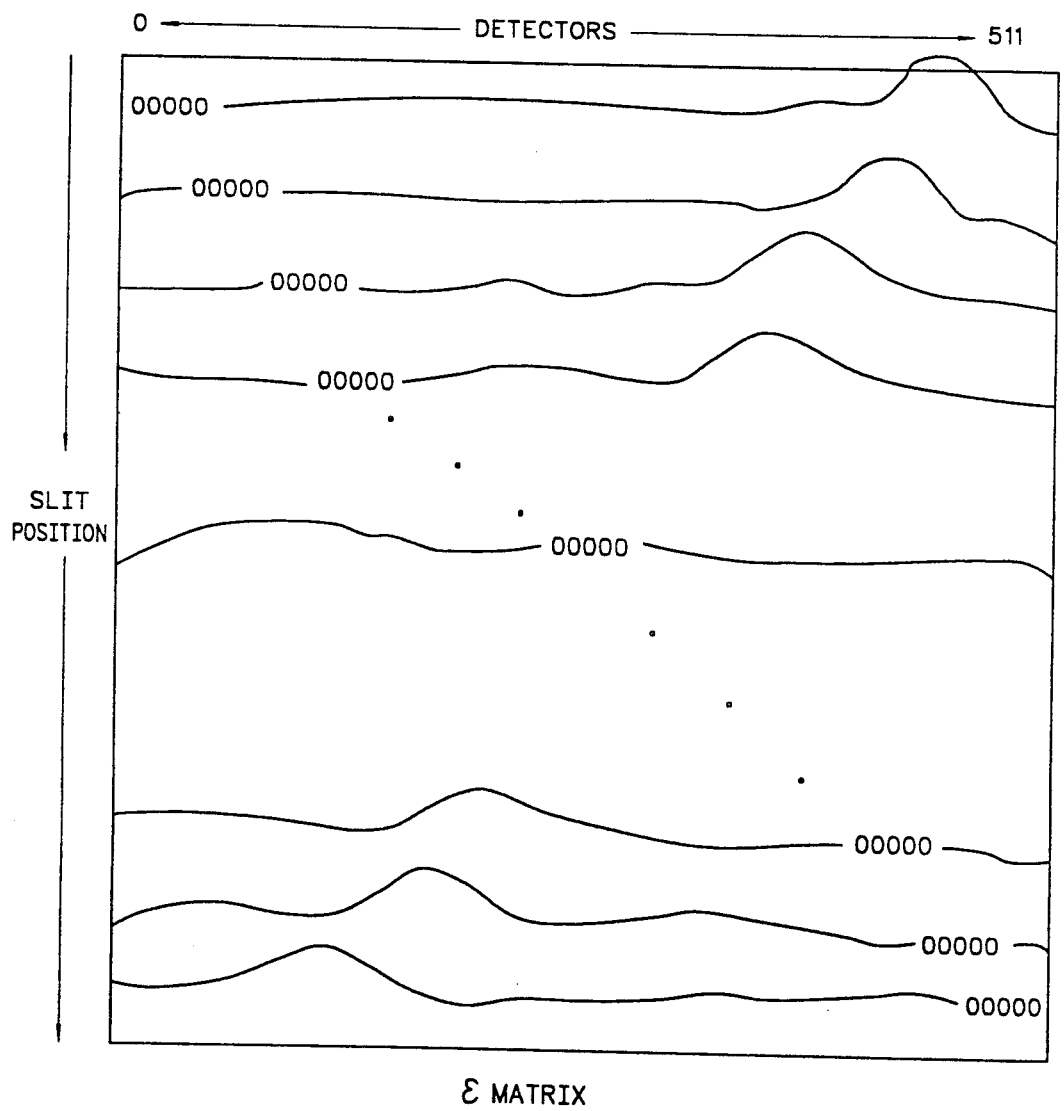
FIG. 25 illustrates what the data might look like after the real peaks have been zeroed out.

In step 326, for each slit position, the data corresponding to the real peak is zeroed out, along with 5 to 10 detector readings on either side of the peak. This leaves the "tails" intact, and zeros down the diagonal of the matrix. FIG. 25 illustrates what the data might look like after the real peaks have been zeroed out. For ease of illustration, the remaining data are depicted in continuous curve form, rather than their actual digital values.

In step 328, the readings in each column which remain from step 326 are then divided by the sum of the readings which were zeroed out for that column. This forms what will be referred to as an "$\epsilon$ matrix."

In practice, when a single detector is illuminated, the resulting point spread function tail is a very small number. In order to obtain a "tail" magnitude which is more accurately measured, several adjacent detectors are illuminated at any particular slit position. The division step in step 328 accounts for the illumination of more than one detector at a time. The manner in which the $\epsilon$ matrix is used to correct the measurement data for the point spread function effect is described in greater detail hereinbelow in connection with step 390, FIG. 26.

Merging Imaging Extension Detector Array 45

Measurements from imaging extension detector array 45 are combined with those from photodiode linear array 44 to provide 544 measurements. When the imaging extension detector array 45 is added to the image intensifier tube 40, its first photodiode is positioned to overlap the last several photodiodes in the photodiode linear array 44. The detector spacing of the photodetectors in the imaging extension detector array 45 is approximately five times that of the effective detector spacing in the photodiode linear array 44. However, this lower spatial resolution is not significant because high spatial content objects are typically not viewed at the periphery of a body scan circle.

As was the case with measurements from the photodiode linear array 44, values can be obtained which correspond to the desired uniform angular displacement for measurements by the imaging extension detector array 45 by interpolating the actual measurement data. These interpolated values are then moved into the correct "expected detector" slots ready for further processing and back projection.

Dual Sample Interval Measurement Method

As is discussed hereinabove, to increase the dynamic range of the detector system, two sets of readings are taken for each projection, a long integrate and a short integrate set. The long integrate period is nine half-line cycles (T-periods) long and the following short integrate period is one half-line cycle (T-period) long. This approach gives an extended period in which to count low numbers of photons accurately. If this reading saturates, then the short integrate value can be used, multiplied by a scaling factor to scale it up to generate an equivalent long integrate value. This approach assumes that the detector response is linear. It also importantly preserves photon statistics. When the short integrate is used the detected x-rays are of sufficient number to discard ninety percent of them in the measurement.

This dual sample interval approach thus provides a substantial and significant increase in the dynamic range of the imaging system. By way of example, if the long interval samples have a 16-bit range, the use of the short sample interval extends the measurement range to effectively 19-bits. In the context of the specific example given, the long interval samples would be used for counts up to about 62,000. The short samples would be used for counts between 62,000 and about 500,000. Thus a dynamic range increase of about 3-bits, or a factor of about 9, is achieved by use of the dual sample interval approach of the present invention.

Detector Non-Linearity Correcting Polynomials

In practice, it has been found that the response of the photodetectors in photodiode linear array 44 are slightly non-linear. A simple apparatus for calibrating the photodetector array is used. A photodiode calibration fixture holding a single LED and a single normalization photodiode are employed and mounted over the detector array in place of the second lens 54. The light output from the single LED is directly proportional to the applied current, thus, the response curves for the photodiodes in the linear array 44 can be determined by plotting photodiode response versus current applied to the LED, and is normalized by curve fitting the data against data from the normalization photodiode. The normalizing photodiode can be the same photodiode as used in normalizing detector 66, but without the scintillating crystal.

Figures 27, 28:
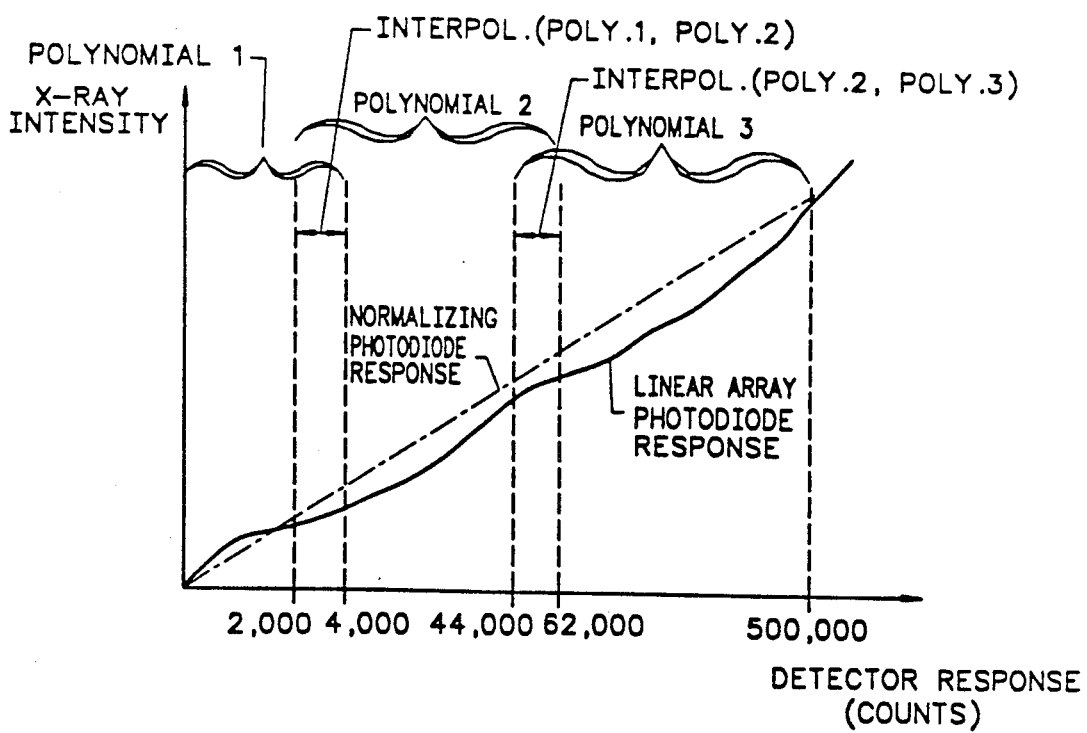
FIG. 27 illustrates a table tabulating photodiode number and coefficient values.
FIG. 28 shows a diagram of polynomial fitting of dose versus measured detector response.

In the preferred embodiment of the present invention, constants $C_0$, $C_1$, $C_2$, $C_3$ and $C_4$ for 4th-order polynomials for each detector are determined and placed in memory during calibration. These constants are used for example in a fourth order polynomial in which the data obtained for each photodiode has been fit to the normalizing photodiode response data using a least-squares curve fit approach. That is, calibration data is obtained for the normalizing photodiode. This data is assumed linear. Then calibration data for each of the photodiodes in linear array 44 is obtained. The calibration data from the photodiodes in linear array 44 is then curve fit to the normalizing photodiode calibration data using a least squares curve fit criteria. FIG. 27 illustrates a table tabulating photodiode number and coefficient values.

A polynomial rather than table lookup is used because the polynomial is continuous and can be conveniently executed in the array processor. The use of a lookup table lookup for the dynamic range found in the present invention would require too much memory and be too slow. While fourth order polynomials are used in the preferred embodiment of the present invention, it is to be understood that polynomials of nth-order, where "n" is more or less than four, can be used within the spirit of the invention.

In the preferred embodiment of the present invention, an adjustment factor is determined prior to curve fitting the calibration data from the photodiodes in the linear array 44 to the calibration data from the normalization photodiode. This adjustment factor permits the non-linearities of the photodiode being curve-fit to be more easily interpreted.

The adjustment factor is determined as follows. The normalization factor is determined for the light intensity level that causes the linear array photodiode to output a particular middle range level, e.g. 40,000 counts. Thus, if a linear array photodiode output ("$d_i$") of 40,000 counts is produced by a light intensity level of $I_0$, and for that same light intensity the normalizing photodetector output ("$n_i$") is 36,000 counts, an adjustment factor, g, is formed by taking the ratio of $n_i$ to $d_i$:

$$\frac{n_i|_{I_0}}{d_i|_{I_0}} = g = \frac{36,000}{40,000}$$

The normalizing photodetector output is always set to be lower than any detector which is being calibrated so that the detector under calibration will staturate before the normalizing detector.

The adjustment factor, g, is then used to multiply the calibration data for the normalizing photodetector, and the calibration data for the linear array photodiodes are curve fit against this adjusted normalizing photodetector calibration data, $n_i^*$. This procedure effectively sets the coefficient for the first order terms in the nth-order polynomial close to "1", thus better revealing the higher order effects. The curve fitting preferably performed for a 4th order polynomial is thus:

$$n_i^* = gn_i = C_0 + C_1 d_i + C_2 d_i^2 + C_3 d_i^3 + C_4 d_i^4$$

where $n_i$ = normalizing photodiode response for light intensity i, $d_i$ = linear array photodiode response for light intensity i, and g = the ratio of $n_i$ for light intensity $I_0$ to $d_i$ for light intensity $I_0$.

In practice it has been found that use of more than one polynomial is useful to describe the response curve of the linear array more accurately because of the manner in which the response curve varies with dose, see FIG. 28. It has been determined that it is more accurate and faster to use a number of higher (e.g. fourth) order polynomials to model the response curve rather than to try and find a single higher order polynomial.

In the current embodiment, one polynomial accurately describes the curve below about 4000 counts and a second polynomial is used from about 2000 to about 62,000 counts. A third is used above about 44,000 counts. See FIG. 28. Corrected values between 2000 and 4000 counts are obtained by applying both polynomials 1 and 2, then interpolating a final result. Corrected values between 44,000 and 62,000 counts are obtained by applying polynomials 2 and 3, then interpolating a final result. In practice, polynomial 1 is used with data below 4,000 counts; polynomial 2 is used with data between 2,000 and 62,000 counts; and polynomial 3 is used with data above 44,000 counts. The overlapping portion of these polynomials is used to determine the values in the transitional ranges 2000 to 4000, and 44,000 to 62,000 by interpolation. This provides smooth transition between one polynomial and the next.

Scaling Factor Determination

Figure 29:
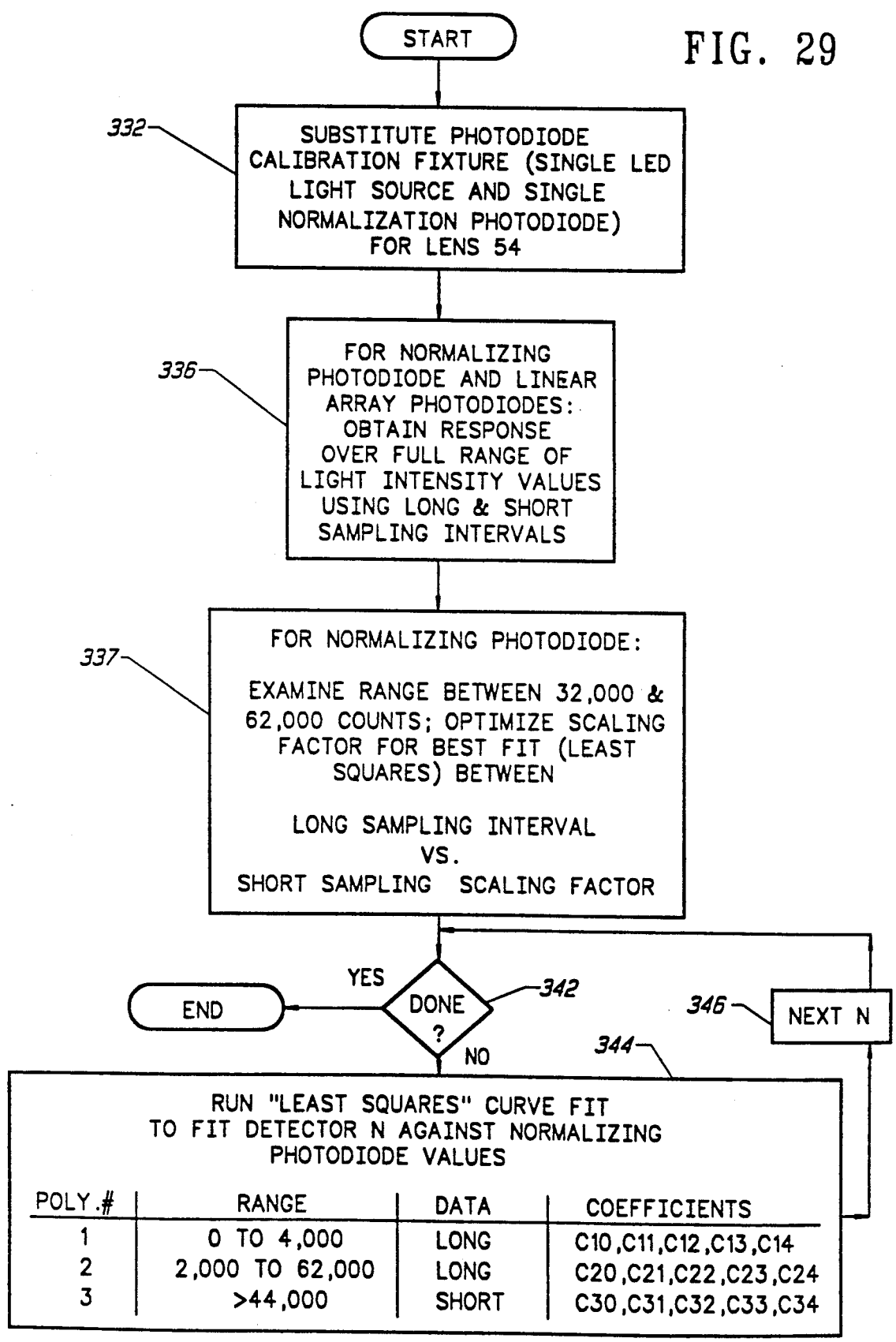
FIG. 29 illustrates a procedure for determining the coefficients for three 4th-order polynomials which correct for non-linearities in the photodiode response.

FIG. 29 illustrates a procedure for determining the coefficients for the three polynomials. In step 332 the photodiode calibration fixture (not shown) having the single LED light source and the single normalization photodiode is substituted for lens 54, FIG 1. In step 336 the response of the photodiode normalization detector and the photodiodes in the linear array 44 is determined over the full range of the expected light intensity values. For each intensity level used, a long and a short sampling interval is used to obtain a long and a short measurement.

Next, in step 337 the scaling factor (for multiplying the short interval) is determined as follows using the data from the normalizing photodiode. The long and short interval measurements are examined in the range between about 32,000 and 62,000 counts. The short measurements are multiplied by a scaling factor which is optimized by least squares fit to obtain the best fit between the long sample measurements and the scaled short sample measurements in that range. The optimized scaling factor is then stored for use in multiplying the short sample measurements for the normalizing photodiode.

In the preferred embodiment of the present invention, the scaling factor is a two-part factor as follows. The relationship between the normalizing photodiode long sample interval measurements ("$L_i$") and short sample interval measurements ("$S_i$") is characterized by the equation:

$$L_i(1 + \alpha L_i) = \kappa S_i.$$

The constants $\alpha$ and $\kappa$ are optimized for the best fit over the count range from about 40,000 to 60,000. That is, for the light intensity values that produce values for $L_i$ in the 40,000 to 60,000 range, the values for $L_i$ and corresponding values for $S_i$ are applied to the above equation and the constants $\alpha$ and $\kappa$ are optimized for best least squares fit.

Once the constants $\alpha$ and $\kappa$ are determined, the calibration values, $n_i$, for the normalizing photodiode, which are to be used in selecting coefficients for linearizing the photodiodes in linear array 44 (step 344), are defined as $$n_i = L_i(1 + \alpha L_i), L_i < 60,000;$$
$$= \kappa S_i, L_i \geq 60,000.$$

Typical values for $\alpha$ are on the order of $10^{-7}$, and for $\kappa$ are approximately 9.

Thereafter, in steps 342, 344 and 346, the coefficients for three, fourth-order polynomials are determined for the photodiode measurement values in the linear array 44, one polynomial each for the ranges 0 to 4,000, 2,000 to 62,000, and 44,000 to 500,000, respectively. A "least squares" curve fit is employed. As discussed above, the curve fit is against the calibration data obtained from the normalizing photodiode. It is to be noted that the calibration values, $n_i$, for the normalizing photodiode are provided over the range from 0 to 500,000 counts, with the counts below 60,000 being provided using the long sample interval measurements, $L_i$, multiplied by $(1+\alpha L_i)$ and the counts above 60,000 being provided using the short sample interval measurements, $S_i$, multiplied by the constant $\kappa$.

The determination of the constants for the 4th-order polynomial for the 44,000 to 500,000 count range is made using the normalizing photodetector value $\kappa S_i$ and the unscaled short sample interval measurement for the particular photodiode from the linear array 44. Because of this, the coefficients $C_{30}$, $C_{31}$, $C_{32}$, $C_{33}$ and $C_{34}$ will effectively incorporate the scaling factor $\kappa$. Recall that the scaling factor $\kappa$ adjusts the magnitudes of the short sample interval measurements to the order of the long sample interval measurement, and in doing so effectively increases the dynamic range of the detection system by 3-bits. In the above manner, the increase in dynamic range is passed on to the measurements made by the photodiodes in the linear array 44. These coefficients are then saved for later use.

In step 344 the coefficients $C_{10}$, $C_{11}$, $C_{12}$, $C_{13}$, and $C_{14}$ correspond to polynomial 1; the coefficients $C_{20}$, $C_{21}$, $C_{22}$, $C_{23}$, and $C_{24}$ correspond to polynomial 2; and the coefficients $C_{30}$, $C_{31}$, $C_{32}$, $C_{33}$, and $C_{34}$ correspond to polynomial 3.

It is to be understood that in determining these coefficients, the long sample interval measurements are used for polynomials 1 and 2. For polynomial 3 the short sample interval measurements are used. These short measurements are fit against the normalizing photodiode measurements which can be long interval measurements, or short interval measurement which have been multiplied by the scaling factor.

SYSTEM OPERATION

Data Collection and Correction

Figure 26:
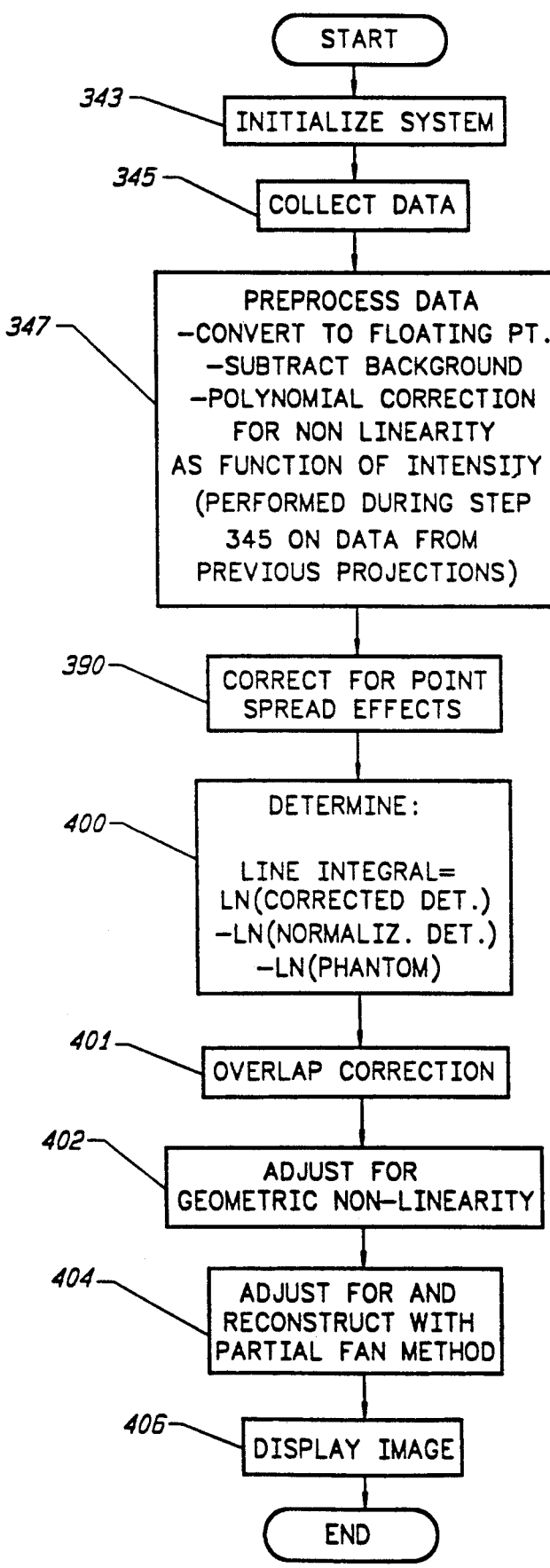
FIG. 26 shows the overall sequence of data collection and correction.

Referring to FIG. 26, the overall sequence of data collection and correction is shown when the system is scanning a patient. After the system is initialized, step 343, data is collected in step 345.

During data collection the readings obtained at every projection are: Projection number; Short sampling interval value; Short normalizing detector value; Long sampling interval value; Long normalizing detector value; and gantry angular position.

Corrected detector data is determined in step 347, FIG. 26. In accordance with the preferred embodiment of the present invention, processing of the actual detector readings is performed while a scan is in process. Because a scan typically takes about a minute to complete, a significant amount of processing of the data can be done during the scan.

As data is received from each projection during a scan the data is converted to floating point and the background level is subtracted from each detector reading. The coefficients for each of the three polynomials are then retrieved. Prior to solving the three polynomials, projection averaging is run to obtain one set of projection readings per degree of gantry rotation. This involves appropriately weighting the projection data taken at angles close to the angle for which the projected data is desired. As discussed earlier, data for two projections per degree are taken; i.e., approximately 720 projections per 360 degrees of rotation in a 60 Hz system. The projection averaging reduces the number of projections to about 360, and thus reduces the computational load. For example, projection for gantry angle 321.5°, 322°, and 322.5° might be averaged together to obtain a set of data for a projection 322°.

Once projection averaging is completed, polynomials 1 and 2 are solved using the long sample interval measurement, and polynomial 3 is solved using the short sample interval measurement.

---

POLYNOMIAL 1:
$DET.' = C_{10} + C_{11}*DET. + C_{12}*DET.^2 + C_{13}*DET.^3 + C_{14}*DET.^4$,
where DET. = Long sampling interval value.
POLYNOMIAL 2:
$DET.' = C_{20} + C_{21}*DET. + C_{22}*DET.^2 + C_{23}*DET.^3 + C_{24}*DET.^4$,
where DET. = Long sampling interval value.
POLYNOMIAL 3:
$DET.' = C_{30} + C_{31}*DET. + C_{32}*DET.^2 + C_{33}*DET.^3 + C_{34}*DET.^4$,
where DET. = Short sampling interval value.

---

DET.' is the CORRECTED DETECTOR value being calculated. In practice, the coefficients for polynomial 3 will incorporate the scaling factor so that the short sample interval measurement need not be multiplied prior to being plugged into polynomial 3.

Figure 30A:
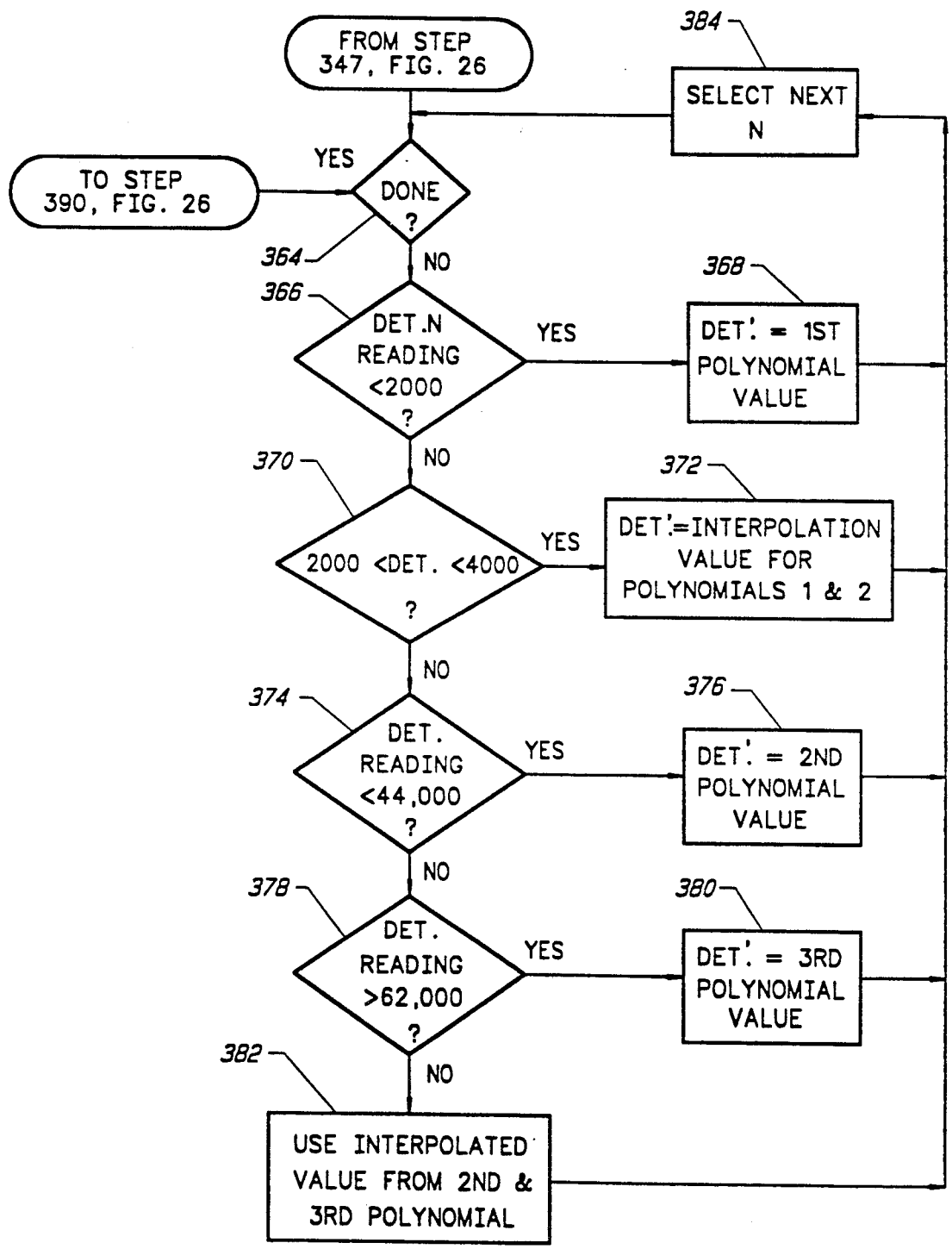
FIG. 30A illustrates the correction of the detector readings using the three polynomials illustrated in FIG. 29.

Conceptually, referring to FIG. 30A, the magnitude of the measurement DET. which is plugged into the polynomials will determine which polynomial result will be actually used for DET'. Steps 364, 366, and 368 illustrate that the result from polynomial 1 will be used for DET.' when DET. is less than 2,000. From steps 370 and 372, it can be seen that the interpolated valves from polynomials 1 and 2 will be used for DET.' when DET. is between 2,000 and 4,000. When DET. is less than 44,000, but greater than 4,000, steps 366, 370, 374, and 376, the from polynomial 2 will be used for DET.'. For DET. values greater than 62,000, steps 378 and 380, the results from the polynomial 3 will be used for DET.' Finally, when DET. is between 44,000 and 62,000, steps 374, 378, and 382, the interpolated values from polynomials 2 and 3 are used for DET.' This procedure is run for the measurements from each photodiode in the linear array 44.

The particular order of processing can be selected to increase processing speed by taking advantage of the array processor characteristics. Thus, in the present embodiment, it is faster to run all three polynomials on the data, rather than to screen the data first to determine the proper range and polynomial, then run the polynomial.

Figure 30B:
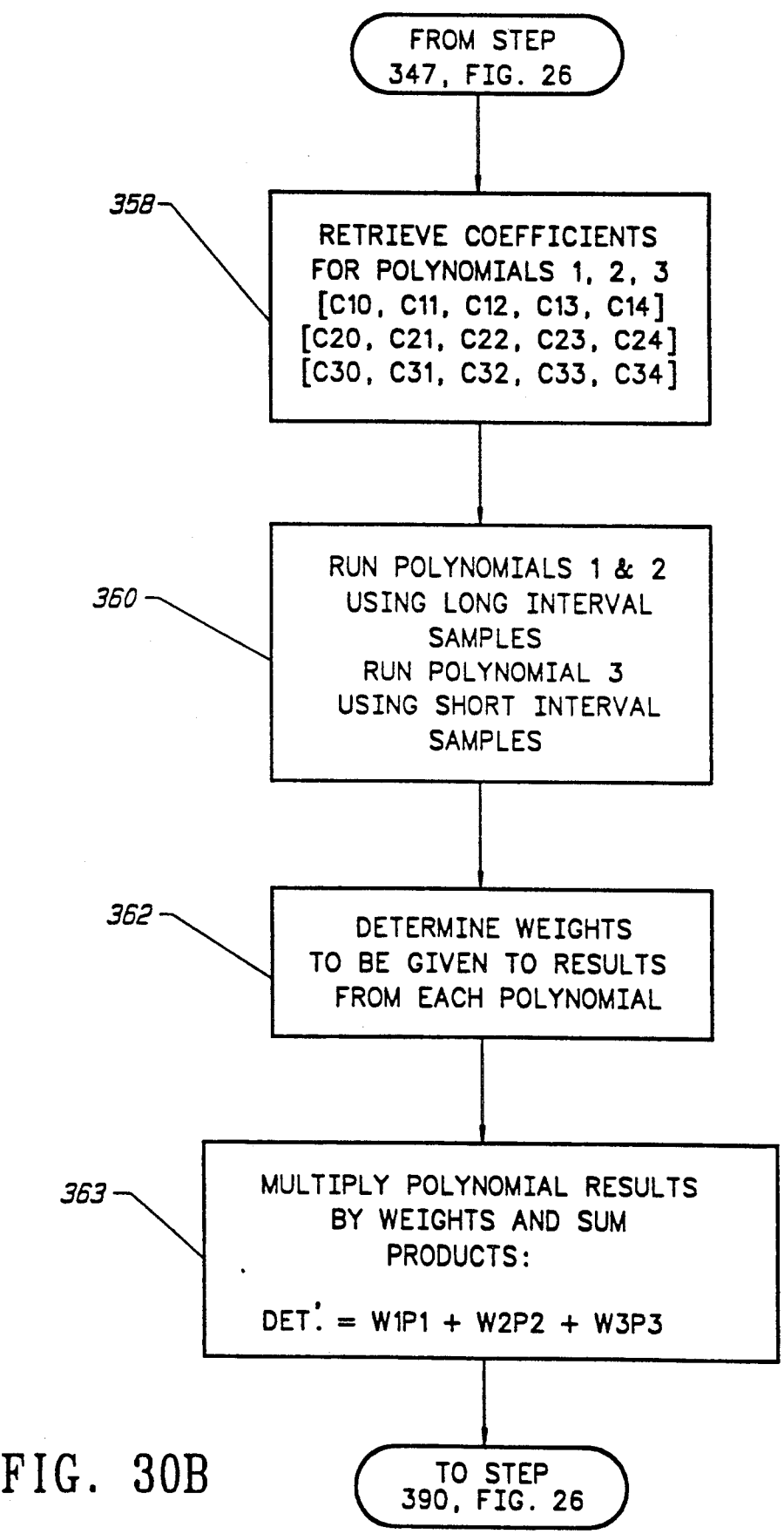
FIG. 30B illustrates the correction of the detector readings according to the preferred method of the present invention in which the results of each polynomial are weighted, and the sum of the weighted polynomial then used as the corrected detector reading.
Figure 30C:
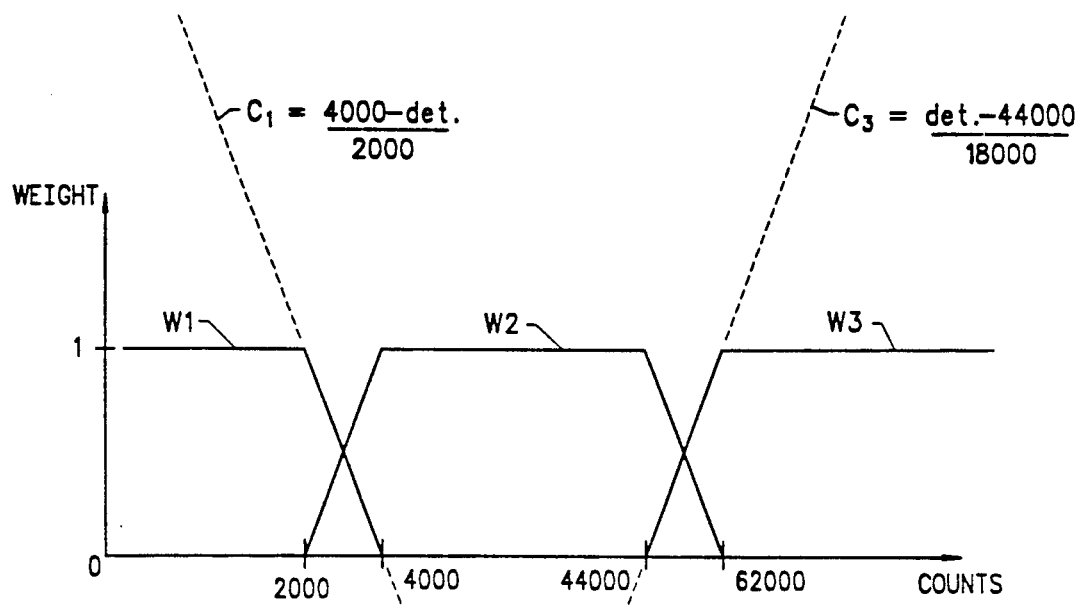
FIG. 30C illustrates the weighing function used in FIG. 30B, for one example of count ranges.

In the present embodiment of the invention, where an array processor is used, a different order of processing is used. See FIG. 30B. Because the IF-THEN operations of steps 366, 370, 374, and 378, FIG. 30A, are operationally intensive, resort has been made to a weighting scheme to increase computational speed. Referring to FIGS. 30B and 30C, this weighting scheme will now be described.

In FIG. 30B, step 358, the coefficients for the three polynomials are retrieved. In step 360, the polynomials 1 and 2 are run using the long sample interval values for the photodiode from the linear array 44, and polynomial 3 is run using the short sample interval valve. In step 362, the "weights" $W_1$, $W_2$, $W_3$, for each of the three polynomials are determined as a function of the magnitude of the long sample interval value. Then, in step 363, the results from each of the three polynomials, $P_1$, $P_2$, and $P_3$, are multiplied by their corresponding weights, then summed to provide the linearized detector value, DET.':

$$DET.' = W_1 P_1 + W_2 P_2 + W_3 P_3.$$

In FIG. 30C, the determination of weights $W_1$, $W_2$, and $W_3$ is shown. The vertical axis represents the weight assigned, while the horizontal axis represents the long sample interval count. In this particular example, the count range is 0 to 500,000. The transitions between polynomials occur at 2000 to 4000 and at 44,000 to 62,000 counts. The weighting factor, $W_1$, for polynomial 1 covers the count range from 0 to 4000 counts, with a break point at 2000 counts. The weighting factor, $W_2$, for polynomial 2, covers the count range from 2,000 to 62,000, with breaks at 4,000 and at 44,000. Finally, the weighting factor $W_3$, for polynomial 3, covers the count range from 44,000 to 500,000. A curve, $C_1$, is defined using the region of weighting factor $W_1$ from 2000 counts to 4000 counts:

$$C_1 = \frac{4000 - DET.}{2000}$$

where DET. equals the long sample interval value. A second curve, $C_3$, is defined. Using the region of weighting factor $W_3$ from 44,000 to 62,000 counts:

$$C_3 = \frac{DET. - 44000}{18,000}$$

$C_1$ and $C_3$ are both solved for each value of DET. that is processed, however, values of $C_1$ and $C_3$ above 1 and below 0 are clipped, i.e., ignored. The weights $W_1$, $W_2$, and $W_3$ are then designated as follows using the values of $C_1$ and $C_3$ for the particular DET.:

$$W_1 = \begin{matrix} 0, & C_1 < 0; \\ 1, & C_1 > 1; \\ C_1, & 0 \leq C_1 \leq 1. \end{matrix}$$

$$W_3 = \begin{matrix} 0, & C_3 < 0; \\ 1, & C_3 > 1; \\ C_3, & 0 \leq C_3 \leq 1. \end{matrix}$$

$$W_2 = 1 - W_3|_{DET.} - W_1|_{DET.}$$

The use of these weights, $W_1$, $W_2$, and $W_3$, in the above manner makes efficient use of the array processor, and increases the speed by which the data can be processed.

Point Spread Function Correction

Returning to FIG. 26, following the correction of the data for background noise and non-linearities, step 347, PSF corrections are made in step 390.

Figure 32:
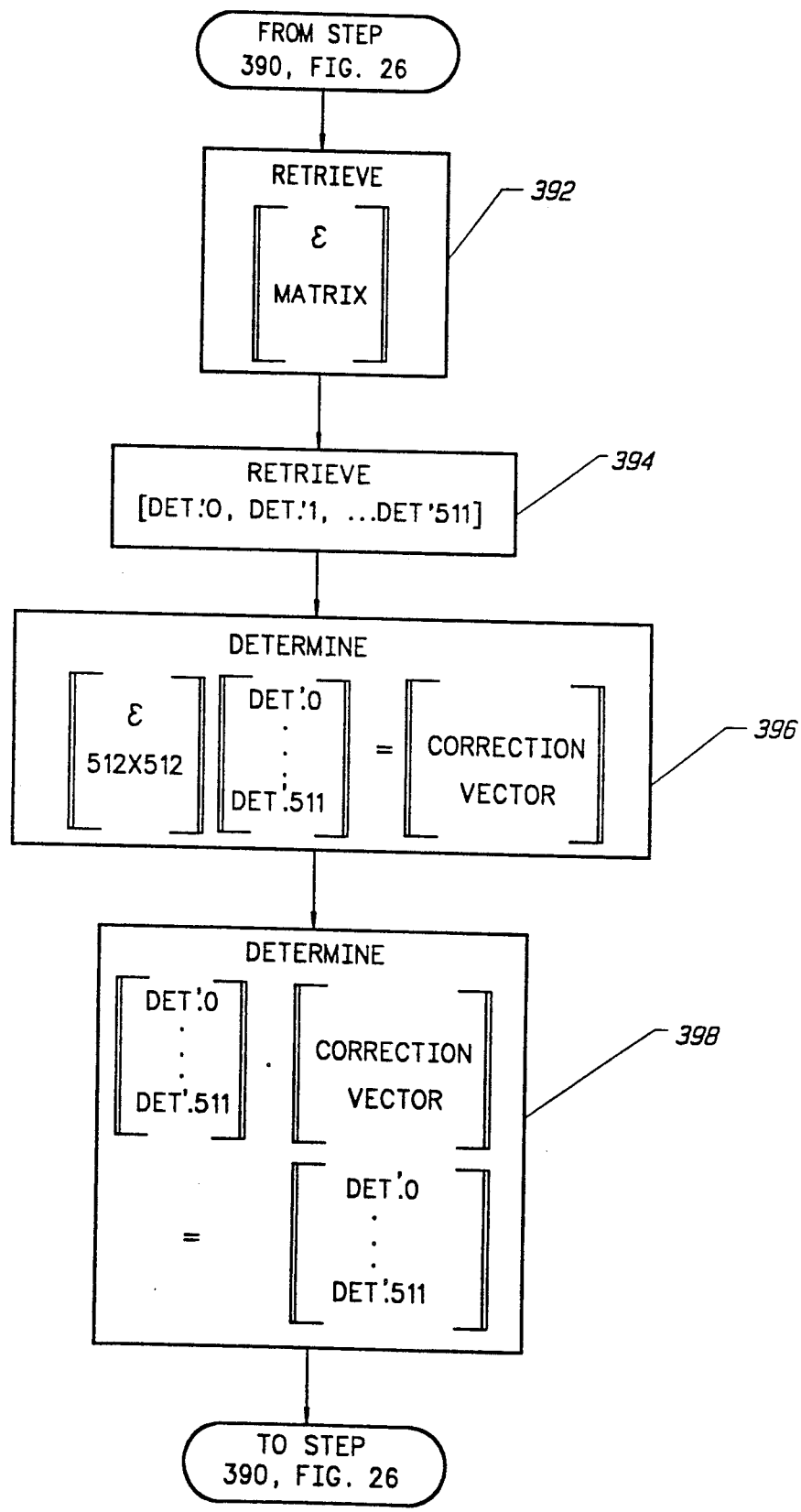
FIG. 32 illustrates the manner in which the $\epsilon$ matrix, illustrated in FIGS. 24 and 25, is used to implement the deconvolution which corrects for the PSF.

In FIG. 32, the $\epsilon$ matrix, discussed above in connection with FIGS. 24 and 25, is used as follows to implement the deconvolution which corrects for the PSF. Assume the following relationship:

$$[A][I] = [R]$$

where, [A] is a 512×512 matrix representing the point spread function, [1] is a 512 element vector representing the x-ray intensity incident on the image intensifier tube face 24 for each of the 512 detectors, and [R] represents the actual measurements from each of the 512 linear array photodiodes taken during a projection. The vector [I] is the information that is being sought. To obtain [I], the vector [R] is multiplied by the inverse of [A], $[A]^{-1}$:

$$\begin{aligned} [A]^{-1}[R] &= [A]^{-1}[A][I] \\ &= [I] \end{aligned}$$

Note, however, that [A] can be expressed as identity matrix plus the $\epsilon$ matrix. Note also that, since the $\epsilon$ matrix is small, $[A]^{-1}$ equals, to a first order, the identity matrix minus the $\epsilon$ matrix.

Thus, in accordance with the preferred embodiment of the present invention, the deconvolved values [I] for the measured data are determined by the equation:

$$[I] = ([IDENTITY\ MATRIX] - [\epsilon\ MATRIX])[R].$$

In step 392, FIG. 32, the $\epsilon$ matrix is retrieved from memory. In step 394, the DET.' values ("[R]"), from step 347, FIG. 26, are retrieved. Then, in step 396 the correction vector is determined by multiplying the DET.' values by the $\epsilon$ matrix. Finally, in step 398, the correction vector is subtracted from the DET.' values to obtain the vector [I], [DET. "0, DET." 1, . . . DET."511].

In accordance with the preferred embodiment of the present invention, the assumption that the PSF is a slowly varying function of position is further exploited to speed up the above identified calculations. Instead of determining the $\epsilon$ matrix for all 512 slit positions, values are collected for every fourth or so position. Thus, the $\epsilon$ matrix might initially take the form of a 128×128 matrix. Further, actual measurements are taken for the corresponding 128 detectors, and the vector [I] is then calculated from this more limited set of data. Because the PSF is a slowly varying function of position, the resulting 128 element [I] vector can be interpolated to a full 512 element vector with minimal loss of resolution.

Phantom Normalization and Line Integral Calculation

Returning to FIG. 26, step 400 is next processed. This step involves a determination of the relationship:

*Line Integral = ln(Corrected DET.) − ln (normaliz. DET.) − ln(phantom).*

The line integral difference is conventional in the computerized tomography scanner art, and involves taking the difference between the natural logarithm of the intensity measured during an actual projection and the intensity measured by the normalizing photodiode and the intensity using a phantom having known absorption characteristics.

Overlap Correction

Figure 31:
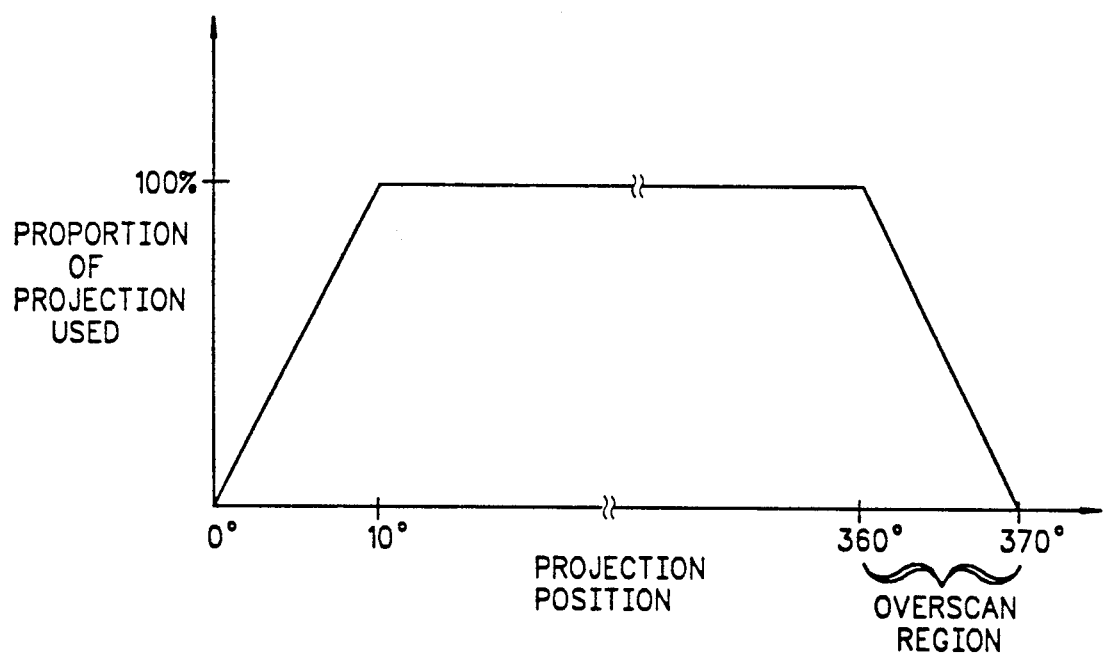
FIG. 31 illustrates the weight assigned to the data from each projection for overlay projection corrections.

There can be approximately 800 projections (60 Hz system) or 650 projections (50 Hz system) worth of data to store. In practice, the gantry is rotated 5 to 10 degrees beyond TDC at the end of a scan. This results in a slight overscan. Projections are taken during this overscan region. Data from these projections are blended with data from projections taken at the beginning of the scan. See FIG. 26, step 401. Referring to FIG. 31, the weighting assigned to the data from each projection is illustrated. From the figure it can be seen that the data taken in the early projections, around zero degrees gantry angle, are lightly weighted, while the data taken at the end of the scan, around 360 degrees, are weighted more heavily and then decreasing in weight out to 370 degrees.

Geometric Non-Linearity Adjustment:

Next, step 402 is processed in which adjustments are made to compensate for geometric or spatial non-linearities. As described in connection with FIGS. 33a, 33b, 33c, and 21, hereinabove, rays in the partial fan-beam which are separated by uniform angles do not necessarily produce responses at detectors in the photodiode linear array 44 which are spaced a correspondingly uniform distance apart.

Figures 21, 22:
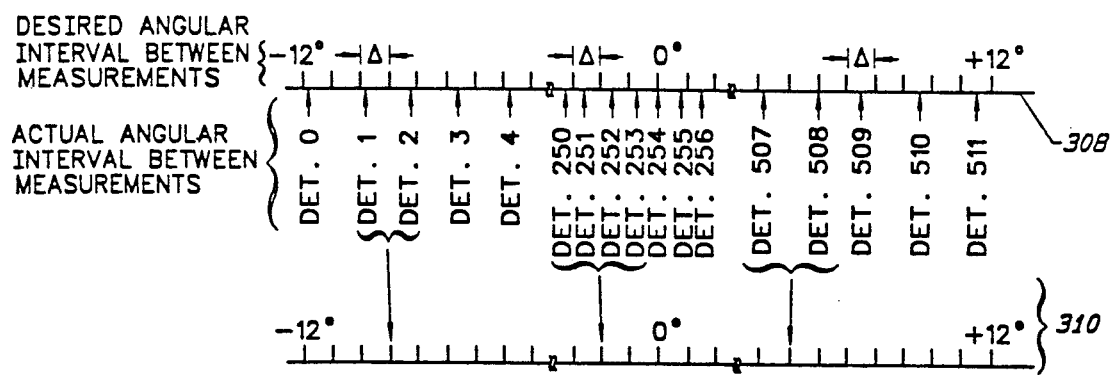
FIG. 21 illustrates a table in which is tabulated the angle of the occluded ray, and the detector which responded to the occluded ray.
FIG. 22 illustrates the manner in which the information tabulated in FIG. 21 is used in connection with actual measurement data.

FIG. 22 illustrates the averaging/interpolation technique employed in step 402, FIG. 26, which corrects for these spatial non-linearities. The upper section of axis 308 illustrates the desired uniform angular interval between measurements, for example, a measurement every Δ degrees, between ±12 degrees. The bottom section of axis 308 illustrates the actual angular interval between the actual measurements. Note that due to the spatial non-linearities in the imaging system detector responses occur at other than the required angles.

As can be seen from portion 310 of FIG. 22, intensity values for a desired angular position are determined by selecting a subset of the detector measurements and interpolating those measurements. Thus, for example, the intensity value for the angular position three-Δ intervals from the −12° point might be determined by interpolating the measurements from detectors 1 and 2. Similarly, the intensity value for the angular position two-Δ intervals to the left of the 0° position might be determined by interpolating the measurements from detectors 250–253. In the above manner, responding detector readings can be averaged/interpolated together and then moved into the correct "required detector" slots ready for further processing and back projection.

The corrected data is then written to a reconstructor input file where it adjusted for partial fan reconstruction and is then ready for partial fan reconstruction, step 404, FIG. 26. Reference is made to co-pending patent application, entitled "Partial Fan-beam Tomographic Apparatus and Data Reconstruction Method", in the names of John Pavkovich and Edward Seppi, and filed even date herewith, in which the adjustment and partial fan reconstruction method are described in detail. This copending application is hereby incorporated herein by reference.

A full print-out of a computer program which implements the present invention in connection with a CT simulator system is provided in Microfiche Appendix A herein.

One immediate result of the wide dynamic range provided by the present invention is that a CT simulator system can be provided in which images are produced which are calibrated to CT numbers. Unlike other previous CT simulator systems, which produced signals calibrated to arbitrary numbers, the CT simulator system according to the invention provides data which is calibrated to CT numbers covering the scale of −1000 to +3000, as in conventional diagnostic CT scanners. To perform such calibration, a phantom of known materials is scanned and the transmission values obtained for each of the materials is stored. When transmission data from an actual scan is obtained, such data is compared against the values obtained for the phantom and appropriate adjustments are made to the data.

This invention is not limited to the preferred embodiment and alternatives heretofore described, to which variations and improvements may be made, without departing form the scope of protection of the present patent and true spirit of the invention, the characteristics of which are summarized in the following claims.

What is claimed is:

1. A method for improving the dynamic resolution of an imaging system comprising a dual exposure technique, including the steps of:
   a. during a first period of time, sampling a visible light output from an image intensifier using a semiconductor photodetector array to provide a short interval count, wherein the photodetector array comprises a plurality of photodiodes;
   b. during a second period of time longer than said first period of time, sampling the visible light output from the image intensifier using the semiconductor photodetector array to provide a long interval count;
   c. selecting the short interval count for further processing, and multiplying the short interval count by a scaling factor, when it is determined that the long interval count falls above a transition range of counts;
   d. selecting the long interval count for further processing when it is determined that the long interval count falls below the transition range of counts;
   e. selecting a weighted combination of the long and short interval counts when the long interval count falls within the transition range of counts, wherein the scaling factor is selected by characterizing a normalizing photodiode according to the steps of:
   i) applying a series of calibrating signals;

ii) measuring the normalizing photodiode response to the series of calibrating signals over a long sample interval and a short sample interval, wherein the calibrating signals have a maximum intensity which is selected so that the normalizing photodiode does not saturate during the long sample interval;

iii) comparing the long sample interval measurements to the short sample interval measurements over a predetermined range of counts, wherein the short sample interval measurements are multiplied by the scaling factor; and iv) adjusting the scaling factor to obtain the best match using a "least squares" curve fitting criteria between the scaled short sample interval measurements and the long sample interval measurements.

2. The method of claim 1, further including the step of linearizing the count selected for further processing for non-linearities in the photodetector array response.

3. The method of claim 2, wherein the linearizing step comprises the steps of:

i) solving a plurality of nth-order polynomials as a function of the selected count, wherein the nth-order polynomials have coefficients which are a function of selected characteristics of the photodetector array, and further wherein different ones of the nth-order polynomials are valid over different count ranges;

ii) selecting an nth-order polynomial which is valid for the count range which includes the selected count; and iii) using the solution of the selected nth-order polynomial as the linearized selected count.

4. The method of claim 3, wherein the nth-order polynomials are valid for ranges of magnitudes of the normalizing photodiode response which overlap, and further wherein the linearizing step includes the further steps of:

iv) determining whether the selected count falls in any of the overlap ranges;

v) interpolating the solutions from the nth-order polynomials which are valid for the overlap range in which the selected count falls; and vi) providing the interpolated solution as the linearized selected count when the selected count falls within that overlap range.

5. The method of claim 3, wherein the coefficients of the nth-order polynomials are selected according to the steps of:

f. applying calibrating signals;

g. measuring the photodetector array response to the calibrating signals;

h. selecting the coefficients for the nth-order polynomials to provide a best fit of the polynomial to the applied calibration signals as a function of the photodetector array response, according to a least squares curve fitting criteria.

6. The method of claim 5, wherein the range of magnitudes of the photodetector array response to the calibrating signals is from zero counts to 500,000 counts and the solving step i) uses solutions from three fourth-order polynomials.

7. The method of claim 6, wherein the zero to 500,000 count range is divided into three ranges, and each of the three fourth-order polynomials is valid for a different one of the three ranges.

8. The method of claim 7, wherein the three ranges overlap.

9. The method of claim 1, wherein the transition range of counts covers a single selected count.

10. The method of claim 1, wherein the scaling factor is a two-part factor characterized by the equation:

$$L_i(1 + \alpha L_i) = \kappa S_i.$$

wherein $L_i$ = the normalizing photodiode long sample interval measurements, $S_i$ = the normalizing photodiode short sample interval measurements, and the constants $\alpha$ and $\kappa$ are optimized for the best fit over the selected range.

* * * * *